US011655268B2

(12) United States Patent
Kim et al.

(10) Patent No.: US 11,655,268 B2
(45) Date of Patent: May 23, 2023

(54) NUCLEOSIDE OR NUCLEOTIDE DERIVATIVES, AND USES THEREOF

(71) Applicant: ST Pharm Co., Ltd., Siheung-si (KR)

(72) Inventors: Kyungjin Kim, Siheung-si (KR); Meehyein Kim, Daejeon (KR); Uk-Il Kim, Siheung-si (KR); Yun Young Go, Daejeon (KR); Hwajung Nam, Siheung-si (KR); Hyung Tae Bang, Siheung-si (KR); Jin Soo Shin, Sejong-si (KR); Jihye Yoon, Siheung-si (KR); Yejin Jang, Daejeon (KR)

(73) Assignee: ST PHARM CO., LTD., Siheung-si (KR)

( * ) Notice: Subject to any disclaimer, the term of this patent is extended or adjusted under 35 U.S.C. 154(b) by 0 days.

(21) Appl. No.: 16/963,900

(22) PCT Filed: Jan. 24, 2019

(86) PCT No.: PCT/KR2019/001036
§ 371 (c)(1),
(2) Date: Jul. 22, 2020

(87) PCT Pub. No.: WO2019/147050
PCT Pub. Date: Aug. 1, 2019

(65) Prior Publication Data
US 2021/0040135 A1    Feb. 11, 2021

(30) Foreign Application Priority Data

Jan. 24, 2018  (KR) ........................ 10-2018-0009009

(51) Int. Cl.
C07H 19/067    (2006.01)
(52) U.S. Cl.
CPC ................... C07H 19/067 (2013.01)
(58) Field of Classification Search
None
See application file for complete search history.

(56) References Cited

U.S. PATENT DOCUMENTS

2016/0031927 A1* 2/2016 Ivachtchenko ......... A61P 43/00
514/49
2016/0052952 A1   2/2016 Suo et al.

FOREIGN PATENT DOCUMENTS

| CN | 101781283 | | 7/2010 |
| CN | 105001291 | | 10/2015 |
| CN | 105001291 A * | 10/2015 |
| EP | 2977379 | | 1/2016 |
| JP | H 10-72486 | | 3/1998 |
| JP | 2004-513083 | | 4/2004 |
| JP | 2016-515545 | | 5/2016 |
| KR | 10-2015-0132879 | | 11/2015 |
| WO | 2015-066053 | | 5/2015 |
| WO | 2015-134334 | | 9/2015 |
| WO | 2017158621 | | 9/2017 |
| WO | WO-2017158621 A1 * | 9/2017 | ................ A61P 1/04 |

OTHER PUBLICATIONS

Wada et al., European Journal of Organic Chemistry, 2001, pp. 4583-4593 (Year: 2001).*
Zhang et al., Tetrahedron Letters, 2008, 49(13), pp. 2052-2055. (Year: 2008).*
KIPO, A PCT Search Report & Written Opinion of PCT/KR2019/001036 dated May 9, 2019.
Takeshi Wada et al., "Synthesis and Hybridization Ability of Oligodeoxyribonucleotides Incorporating N-Acyldeoxycytidine Derivatives", European Journal of Organic Chemistry, 2001, 4583-4593.
Mark P. Wallis et al., "Synthesis and anti-HIV activity of C4-modified pyrimidine nucleosides", Il Farmaco, 1999, 54, 83-89.
Hari K. Akula et al., "Facile functionalization at the C4 position of pyrimidine nucleosides via amide group activation with (benzotriazol-1-yloxy)tris(dimethylamino)phosphonium hexafluorophosphate (BOP) and biological evaluations of the products", Organic & Biomolecular Chemistry, Jan. 5, 2017, 15, 1130-1139. DOI: 10.1039/c6ob02334g.
Deyi Zhang et al., "Facile rearrangement of N4-(a-aminoacyl)cytidines to N-(4-cytidinyl)amino acid amides", Tetrahedron Letters, 2008, 49, 2052-2055.
Kyungjin Lee et al., "Gemcitabine, a broad-spectrum antiviral drug, suppresses enterovirus infections through innate immunity induced by the inhibition of pyrimidine biosynthesis and nucleotide depletion", Oncotarget, Dec. 15, 2017, 8, 70, 115315-115325.
Y. Jang et al., 2016. Antiviral activity of KR-23502 targeting nuclear export of influenza B virus ribonucleoproteins, Antiviral Res 134:77-88. DOI: 10.1016/j.antiviral.2016.07.024.
Christine L. Clouser et al., "Activity of a Novel Combined Antiretroviral Therapy of Gemcitabine and Decitabine in a Mouse Model for HIV-1", Antimicrobial Agents and Chemotherapy, p. 1942-1948, Jan. 2012. DOI: 10.1128/AAC.06161-11.
Adriaan H. de Wilde et al., "Screening of an FDA-approved compound library identifies four small-molecule inhibitors of Middle East respiratory syndrome coronavirus replication in cell culture", Antimicrobial Agents and Chemotherapy, May 19, 2014, doi:10.1128/AAC.03011-14.
Hyunju Kang et al., "Synergistic antiviral activity of gemcitabine and ribavirin against enteroviruses", Antiviral Research, vol. 124, p. 1-10, Dec. 2015.
Donata Pluskota-Karwatka et al., "Formation of Malonaldehyde-Acetaldehyde Conjugate Adducts in Calf Thymus DNA" Chemical Research in Toxicology, 2006, vol. 19, pp. 921-926.
Mark P. Wallis et al., Direct synthesis, substitution, and structure of 1-(2'-deoxyβ-D-erythro-pentofuranosyl)-4-pentafluorophenylpyrimidin-2H-one, Tetrahedron Letters, vol. 36, Issue 21, May 22, 1995, pp. 3759-3762.

(Continued)

*Primary Examiner* — Traviss C McIntosh, III
(74) *Attorney, Agent, or Firm* — Lex IP Meister, PLLC

(57) ABSTRACT

The present disclosure relates to a novel nucleoside or nucleotide derivative, a racemate thereof, a stereoisomer thereof, or a pharmaceutically acceptable salt thereof; and a pharmaceutical composition for preventing or treating viral infection-associated diseases, containing the same as an active ingredient.

8 Claims, No Drawings

(56) References Cited

OTHER PUBLICATIONS

Ken Yamada et al., "A new modified cytosine base capable of base pairing with guanine using four hydrogen bonds", Organic & Biomolecular Chemistry, 2014, vol. 12, pp. 2255-2262.

A. Kraszewski et al., "Synthesis of 4-mono- and dialkyl-2'-deoxycytidines and their insertion into an oligonucleotide", Tetrahedron Letters, vol. 27, No. 7, Jan. 1, 1986 pp. 861-864.

Thomas R. Webb et al., "Hybridization triggered cross-linking of deoxyoligonucleotides", Nucleid Acids Research, Oxford University Press, GB, vol. 14, No. 19, Oct. 1, 1986.

Komatsu Hironori et al. "An Efficient Amination Method for Manufacturing Cytidines", Organic Process Research & Development vo. 8, No. 4, May 20, 2004 pp. 564-567.

JPO, Office Action of the corresponding JP Patent Application No. 2020-540631, dated Oct. 5, 2021.

EPO, Search Report of the corresponding European Patent Application No. 19743401.2., dated Oct. 12, 2021.

EPO, Search Report of EP 19743401.2 dated Dec. 23, 2021.

* cited by examiner

NUCLEOSIDE OR NUCLEOTIDE DERIVATIVES, AND USES THEREOF

CROSS-REFERENCE WITH RELATED APPLICATION(S)

This application claims the benefit of Korean Patent Application No. 10-2018-0009009 filed on Jan. 24, 2018 with the Korean Intellectual Property Office, the disclosure of which is incorporated herein by reference in its entity.

TECHNICAL FIELD

The present disclosure relates to a novel nucleoside or nucleotide derivative, a racemate thereof, a stereoisomer thereof, or a pharmaceutically acceptable salt thereof; a pharmaceutical composition for preventing or treating viral infection-associated diseases, containing the same as an active ingredient, and use thereof.

BACKGROUND ART

Nucleoside or nucleotide derivatives have been used in clinical treatment of viral infection or cancer-associated diseases.

The antiviral activity of gemcitabine has been reported against RNA viruses (e.g., influenza virus, enterovirus, SARS and MERS Coronavirus) and retroviruses (e.g., human immunodeficiency virus) (Clouser et al., 2012; Kang et al., 2015, de Wilde et al., 2014). As a result of cell-based antiviral tests, Gemcitabine has shown a broad range of efficacies against influenza viruses (types A and B), enteroviruses (coxsackievirus, poliovirus) and coronaviridae (coronavirus).

However, a broad range of toxicity has been observed against cultured cells, and in the case of Madin-Darby Canine Kidney (MDCK; derived from dog kidney cells) cells, which are used for influenza virus infection, about 50% cell death was induced when administered at a concentration of 100 μM for 3 days.

Therefore, the antiviral efficacy was investigated by synthesizing novel nucleoside or nucleotide derivatives capable of improving the cytotoxicity while maintaining the antiviral activity.

DETAILED DESCRIPTION OF THE INVENTION

Technical Problem

It is an object of the present disclosure to provide a novel nucleoside or nucleotide compound, a racemate thereof, a stereoisomer thereof, or a pharmaceutically acceptable salt thereof which exhibits antiviral activity.

It is another object of the present disclosure to provide a preparation method thereof.

It is yet another object of the present disclosure to provide a pharmaceutical composition for preventing or treating viral infection-associated diseases, which comprises the compound of the present disclosure, the racemate thereof, the stereoisomer thereof, or the pharmaceutically acceptable salt thereof as an active ingredient.

Technical Solution

The present inventors have conducted intensive studies in order to achieve the above objects, and have found that the newly designed and synthesized nucleoside or nucleotide derivatives have antiviral activity, thereby completing the present disclosure.

Hereinafter, the present disclosure will be described in more detail.

Nucleoside or Nucleotide Derivative Compound

According to an embodiment of the present disclosure, there is provided a compound represented by the following Chemical Formula 1, a racemate thereof, a stereoisomer thereof, or a pharmaceutically acceptable salt thereof:

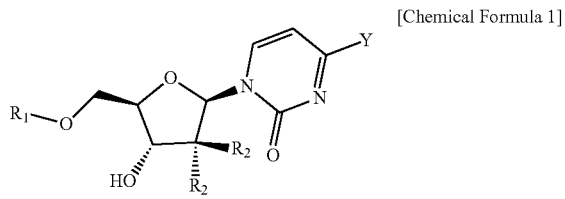

[Chemical Formula 1]

in the Chemical Formula 1,
Y is heterocyclyl or —NHC(O)R$_3$;
R$_1$ is hydrogen or

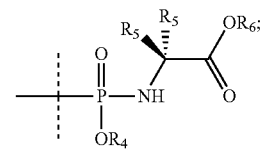

R$_2$ is hydrogen or halo;
R$_3$ is heteroaryl or heterocyclyl (wherein the heteroaryl or heterocyclyl is unsubstituted, or 1 to 4 hydrogens may be substituted with a substituent selected from the group consisting of halo, amino, cyano, nitro, azido, thiol, hydroxy, C$_{1-6}$ alkyl, C$_{1-6}$ haloalkyl, C$_{1-6}$ aminoalkyl, C$_{1-6}$ hydroxyalkyl, C$_{1-6}$ dihydroxyalkyl, C$_{1-6}$ alkoxy, C$_{1-6}$ cycloalkyl, heterocyclyl, C$_{1-3}$ alkoxy-C$_{1-3}$ alkyl and aryl),
R$_4$, R$_5$ and R$_6$ are each independently hydrogen, C$_{1-6}$ alkyl, C$_{1-6}$ haloalkyl, aryl or heteroaryl;
the halo is F, Cl, Br or I;
the heterocyclyl is in the form of a 3- to 10-membered single or fused ring containing one or more heteroatoms selected from the group consisting of nitrogen, oxygen, sulfur or a combination thereof, and the heteroaryl may be in the form of a 5- to 10-membered single or fused ring containing one or more heteroatoms selected from the group consisting of nitrogen, oxygen, sulfur or a combination thereof;
each of the cycloalkyl and the heterocyclyl may be optionally substituted with one to three of C$_{1-6}$ alkyl, hydroxy, oxo, C$_{1-6}$ hydroxyalkyl, halo, cyano, nitro, C$_{1-6}$ haloalkyl, C$_{1-6}$ alkoxy, formyl, C$_{1-6}$ alkylformyl, carboxy, C$_{1-6}$ alkylcarboxy, amino, C$_{1-6}$ alkylamino, di(C$_{1-6}$ alkyl)amino, carbamoyl, C$_{1-6}$ alkylcarbamoyl, di(C$_{1-6}$ alkyl)carbamoyl or C$_{1-3}$ alkoxy-C$_{1-3}$ alkyl; and
each of the aryl and heteroaryl may be optionally substituted with one to three of C$_{1-6}$ alkyl, C$_{1-6}$ alkoxy, C$_{1-3}$ alkoxy-C$_{1-3}$ alkyl, C$_{1-6}$ hydroxyalkyl, C$_{1-6}$ haloalkyl, halo, cyano, pyrazinyl, hydroxy, oxo, nitro, formyl, C$_{1-6}$ alkylformyl, carboxy, C$_{1-6}$ alkylcarboxy, amino, C$_{1-6}$ alkylamino, di(C$_{1-6}$ alkyl)amino, carbamoyl, C$_{1-6}$ alkylcarbamoyl, di(C$_{1-6}$ alkyl)carbamoyl or C$_{1-6}$ alkylsulfonyl.

According to another embodiment of the present disclosure, there is provided the compound of Chemical Formula 1, the racemate thereof, the stereoisomer thereof, or the pharmaceutically acceptable salt thereof, wherein Y is heterocyclyl or —NHC(O)R$_3$;

R$_1$ is hydrogen or

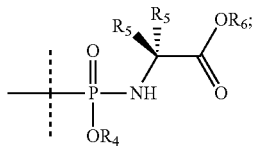

R$_2$ is hydrogen or halo;

R$_3$ is heteroaryl or heterocyclyl (wherein the heteroaryl or heterocyclyl is unsubstituted, or 1 to 4 hydrogens of the heteroaryl or heterocyclyl may be substituted with a substituent selected from the group consisting of halo, amino, cyano, nitro, azido, thiol, hydroxy, C$_{1-4}$ alkyl, C$_{1-4}$ haloalkyl, C$_{1-4}$ aminoalkyl, C$_{1-4}$ hydroxyalkyl, C$_{1-4}$ dihydroxyalkyl, C$_{1-4}$ cycloalkyl, C$_{1-4}$ alkoxy, heterocyclyl, C$_{1-3}$ alkoxy-C$_{1-3}$ alkyl and aryl), R$_4$, R$_5$ and R$_6$ are each independently hydrogen, C$_{1-4}$ alkyl, C$_{1-4}$ haloalkyl, aryl or heteroaryl;

the halo is F, Cl, Br or I;

the heterocyclyl is in the form of a 3- to 10-membered single or fused ring containing one or more heteroatoms selected from the group consisting of nitrogen, oxygen, sulfur or a combination thereof, and the heteroaryl may be in the form of a 5- to 10-membered single or fused ring containing one or more heteroatoms selected from the group consisting of nitrogen, oxygen, sulfur or a combination thereof;

each of the cycloalkyl and the heterocyclyl may be optionally substituted with one to three C$_{1-4}$ alkyl, hydroxy, oxo, C$_{1-4}$ hydroxyalkyl, halo, cyano, nitro, C$_{1-4}$ haloalkyl, C$_{1-4}$ alkoxy, formyl, C$_{1-4}$ alkylformyl, carboxy, C$_{1-4}$ alkylcarboxy, amino, C$_{1-4}$ alkylamino, di(C$_{1-4}$ alkyl)amino, carbamoyl, C$_{1-4}$ alkylcarbamoyl, di(C$_{1-4}$ alkyl)carbamoyl or C$_{1-3}$ alkoxy-C$_{1-3}$ alkyl; and each of the aryl and the heteroaryl may be optionally substituted with one to three of C$_{1-6}$ alkyl, C$_{1-6}$ alkoxy, C$_{1-3}$ alkoxy-C$_{1-3}$ alkyl, C$_{1-6}$ hydroxyalkyl, C$_{1-6}$ haloalkyl, halo, cyano, pyrazinyl, hydroxy, oxo, nitro, formyl, C$_{1-4}$ alkylformyl, carboxy, C$_{1-6}$ alkylcarboxy, amino, C$_{1-4}$ alkylamino, di(C$_{1-4}$ alkyl)amino, carbamoyl, C$_{1-4}$ alkylcarbamoyl, di(C$_{1-4}$ alkyl)carbamoyl or C$_{1-4}$ alkylsulfonyl.

According to yet another embodiment of the present disclosure, there is provided the compound of Chemical Formula 1, the racemate thereof, the stereoisomer thereof, or the pharmaceutically acceptable salt thereof, wherein R$_3$ is pyridinyl, pyrimidinyl, pyrazinyl, pyridazinyl or triazinyl (wherein the pyridinyl, pyrimidinyl, pyrazinyl, pyridazinyl or triazinyl is unsubstituted, or 1 to 4 hydrogens thereof may be substituted with a substituent selected from the group consisting of halo, amino, cyano, nitro, azido, thiol, hydroxy, C$_{1-4}$ alkyl, C$_{1-4}$ haloalkyl, C$_{1-4}$ aminoalkyl, C$_{1-4}$ hydroxyalkyl, C$_{1-4}$ dihydroxyalkyl, C$_{1-4}$ cycloalkyl, C$_{1-4}$ alkoxy, heterocyclyl, C$_{1-3}$ alkoxy-C$_{1-3}$ alkyl and aryl);

the aryl is phenyl;

the heterocyclyl may be tetrahydropyranyl, tetrahydrofuranyl, dihydrofuranyl, dihydropyranyl, dioxanyl, dithianyl, dioxolanyl, imidazolidinyl, imidazolinyl, pyrrolinyl, oxetanyl, pyrrolidinyl, piperidinyl, piperazinyl, morpholinyl, thiomorpholinyl, dioxothiomorpholinyl, dioxotetrahydrothiophenyl, dioxothiolanyl, oxopiperidinyl, oxopyrrolidinyl, oxoimidazolidinyl or oxooxazolidinyl;

the heteroaryl may be tetrazolyl, imidazolyl, pyridinyl, pyridazinyl, pyrimidinyl, triazinyl, pyrrolyl, pyrazolyl, triazolyl, pyrazinyl, furyl, thienyl, isoxazolyl, thiazolyl, isothiazolyl, thiadiazolyl, furazanyl, oxazolyl, indolyl, isoindolyl, indazolyl, quinolinyl, isoquinolinyl, benzothiazolyl, benzooxazolyl, benzofuranyl, benzoimidazolyl, benzotriazolyl or azaindoleyl;

each of the cycloalkyl and the heterocyclyl may be optionally substituted with one to three of C$_{1-4}$ alkyl, hydroxy, oxo, halo or C$_{1-4}$ haloalkyl; and each of the aryl and heteroaryl may be optionally substituted with one to three of C$_{1-4}$ alkyl, C$_{1-4}$ haloalkyl, halo, hydroxy or oxo.

According to a further embodiment of the present disclosure, there is provided the compound of Chemical Formula 1, the racemate thereof, the stereoisomer thereof, or the pharmaceutically acceptable salt thereof, wherein Y is oxopyrrolidinyl, oxoimidazolidinyl or —NHC(O)R$_3$, wherein the oxopyrrolidinyl and oxoimidazolidinyl may be unsubstituted, or 1 to 3 hydrogens thereof may be substituted with a substituent selected from the group consisting of fluoro, methyl and trifluoromethyl;

R$_2$ is hydrogen or fluoro; and

R$_3$ is pyridinyl, pyrimidinyl, pyrazinyl or pyridazinyl (wherein the pyridinyl, pyrimidinyl, pyrazinyl or pyridazinyl is unsubstituted, or 1 to 4 hydrogens thereof may be substituted with a substituent selected from the group consisting of fluoro, chloro, methyl, cyano, nitro, amino, methoxy, trifluoromethyl and phenyl).

According to a further embodiment of the present disclosure, there is provided the compound of Chemical Formula 1, the racemate thereof, the stereoisomer thereof, or the pharmaceutically acceptable salt thereof, wherein Y is oxopyrrolidinyl, oxoimidazolidinyl, nicotinoylamino, picolinoylamino, fluoronicotinoylamino, methylnicotinoylamino, pyridazinylcarbonylamino, fluoropicolinoylamino, methyl picolinoylamino or trifluoromethylnicotinoylamino.

According to one embodiment of the present disclosure, the compound may be selected from the group consisting of:
1) N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide;
2) N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide;
3) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-fluoronicotinamide;
4) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylnicotinamide;
5) N-(1-((2R,4R,5R)-3,3-difluoro-4-hydroxy-5-(hydroxymethyl)tetrahydrofuran-2-yl)-2-oxo-1,2-dihydropyrimidin-4-yl)pyridazine-3-carboxamide;
6) N-(1-((2R,4R,5R)-3,3-difluoro-4-hydroxy-5-(hydroxymethyl)tetrahydrofuran-2-yl)-4-(2-oxoimidazolidin-1-yl)pyrimidin-2(1H)-one;
7) N-(1-((2R,4R,5R)-3,3-difluoro-4-hydroxy-5-(hydroxymethyl)tetrahydrofuran-2-yl)-4-(2-oxopyrrolidin-1-yl)pyrimidin-2(1H)-one;
8) N-(1-((2R,4R,5R)-3,3-difluoro-4-hydroxy-5-(hydroxymethyl)tetrahydrofuran-2-yl)-4-(3-methyl-2-oxoimidazolidin-1-yl)pyrimidin-2(1H)-one;

9) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-fluoropicolinamide;
10) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methylpicolinamide;
11) N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide;
12) N-(1-((2R,4R,5R)-3,3-difluoro-4-hydroxy-5-(hydroxymethyl)tetrahydrofuran-2-yl)-2-oxo-1,2-dihydropyrimidin-4-yl)-3-methylpicolinamide;
13) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylpicolinamide;
14) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-(trifluoromethyl)nicotinamide;
15) N-(1-((2R,4R,5R)-3,3-difluoro-4-hydroxy-5-(hydroxymethyl)tetrahydrofuran-2-yl)-2-oxo-1,2-dihydropyrimidin-4-yl)-1-methyl-1H-pyrazole-4-carboxamide;
16) Isopropyl ((S)-(((2R,3R,5R)-4,4-difluoro-3-hydroxy-5-(4-(nicotinamido)-2-oxopyrimidine-1(2H)-yl)tetrahydrofuran-2-yl)methoxy)(phenoxy)phosphoryl)-L-alaninate;
17) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-phenylpicolinamide;
18) 1-((2R,4R,5R)-3,3-difluoro-4-hydroxy-5-(hydroxymethyl)tetrahydrofuran-2-yl)-4-(3-methyl-2-oxopyrrolidin-1-yl)pyrimidin-2(1H)-one;
19) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-nitropicolinamide;
20) 5-amino-N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide-hydrochloride;
21) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methoxypicolinamide;
22) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methoxynicotinamide;
23) 6-Chloro-N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide;
24) N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methylpyrimidin-4-carboxamide;
25) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-phenylpicolinamide;
26) N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide;
27) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-phenylpicolinamide;
28) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-phenylpicolinamide;
29) N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methylpyrimidin-4-carboxamide;
30) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-nitropicolinamide;
31) 5-Amino-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide;
32) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylnicotinamide;
33) N-(1-((2S,3R,4R,5R)-3-fluoro-4-hydroxy-5-(hydroxymethyl)tetrahydrofuran-2-yl)-2-oxo-1,2-dihydropyrimidin-4-yl)pyridazine-3-carboxamide;
34) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylpyrazine-2-carboxamide;
35) 5-Fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide;
36) N-(1-((2S,3R,4R,5R)-3-fluoro-4-hydroxy-5-(hydroxymethyl)tetrahydrofuran-2-yl)-2-oxo-1,2-dihydropyrimidin-4-yl)pyrimidine-4-carboxamide;
37) 5-cyano-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide;
38) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methylpicolinamide;
39) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methoxypicolinamide;
40) N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide;
41) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-(trifluoromethyl)nicotinamide;
42) 6-Fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide;
43) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methoxynicotinamide; and
44) Isopropyl ((S)-(((2R,3R,4R,5R)-4-fluoro-3-hydroxy-5-(4-(2-methylpyrimidine-4-carboxamido)-2-oxopyridin-1(2H)-yl)tetrahydrofuran-2-yl)methoxy)(phenoxy)phosphoryl)-L-alaninate. However, the present disclosure is not limited thereto.

The compounds of Chemical Formula 1 of the present disclosure may exist in the form of a pharmaceutically acceptable salt, and an acid addition salt formed by a pharmaceutically acceptable free acid is useful as the salt. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

Wherein, an organic acid and an inorganic acid can be used as the free acid. Examples of the inorganic acids include hydrochloric acid, phosphoric acid, sulfuric acid, nitric acid, and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto.

In addition, a pharmaceutically acceptable metal salt can be obtained using a base. At this time, in particular, sodium, potassium or calcium salt are pharmaceutically suitable to be prepared as metal salt, without being limited thereto. In addition, the corresponding silver salt can be obtained by reacting alkali metal or alkali earth metal salt with suitable silver salt (for example, silver nitrate).

As the salts of the nucleoside or nucleotide derivatives of the present disclosure, all types of pharmaceutically acceptable salts can be used without limitation as long as they are salts of nucleoside or nucleotide derivatives that exhibit antiviral activity equivalent to nucleoside or nucleotide derivative compounds.

Preparation Method of Nucleoside or Nucleotide Derivative Compound

The compound of Chemical Formula 1 of the present disclosure can be synthesized from 4-amino-1-((2R,4R,5R)-3,3-difluoro-4-hydroxy-5-(hydroxymethyl)tetrahydrofuran-2-yl)pyrimidine-2(1H)-one or 4-amino-1-((2R,3R,4R,5R)-3-fluoro-4-hydroxy-5-(hydroxymethyl)tetrahydrofuran-2-yl)pyrimidine-2(1H)-one by a series of reactions, and as a specific aspect, it can be prepared according to Reaction Scheme 1 below.

However, Reaction Scheme 1 is only an exemplary method for preparing the compound of the present disclosure, and the method for preparing the compound of the present disclosure is not limited thereto, and may be performed by using a method known in the art or by appropriately changing it.

As described above, one or more reactions known in the art may be further performed from 4-amino-1-((2R,4R,5R)-3,3-difluoro-4-hydroxy-5-(hydroxymethyl)tetrahydrofuran-2-yl)pyrimidine-2(1H)-one or 4-amino-1-((2R,3R,4R,5R)-3-fluoro-4-hydroxy-5-(hydroxymethyl)tetrahydrofuran-2-yl)pyrimidine-2(1H)-one which is the starting material of the compound of the present disclosure, thereby introducing a substituent ($R_3$).

For example, based on Reaction Scheme 1 below, a protection reaction is performed on an alcohol in a compound 1 to synthesize a compound 2, which is subjected to an amide reaction using various carbonyl halides, thereby obtaining a nucleoside derivative compound 3, which is the-desired compound of the present disclosure.

[Reaction Scheme 1]

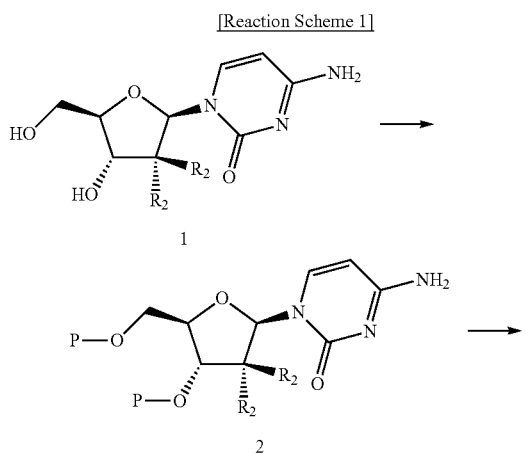

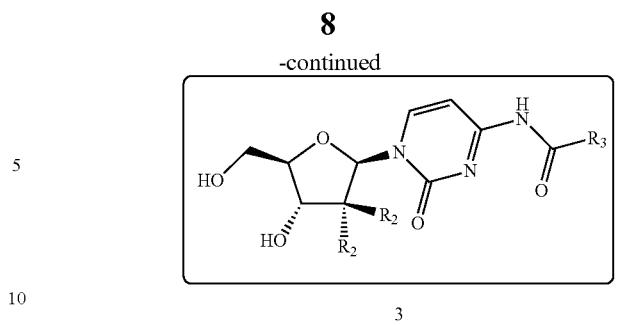

Preferably, various groups conventionally used as a protecting group in the protection reaction can be used as the protecting group (P) without limitation, and in a specific embodiment according to the present disclosure, a trimethylsilyl (TMS) or tert-butyldimethylsilyl (TBS) group is used.

Further, the reaction can be performed by reacting the intermediate 2 with a carbonyl halide containing a substituent ($R_3$) suitable for the desired compound in a pyridine/DCM solvent. Preferably, the reaction may be performed at −78 to 60° C. for 7 to 18 hours.

For example, based on Reaction Scheme 2 below, the phosphoamidite reaction is performed from a compound 4 to synthesize a compound 5, which is then subjected to amide reaction using various carbonyl halides, followed by a deprotection reaction to obtain a nucleotide derivative compound 6 which is the desired compound of the present disclosure.

[Reaction Scheme 2]

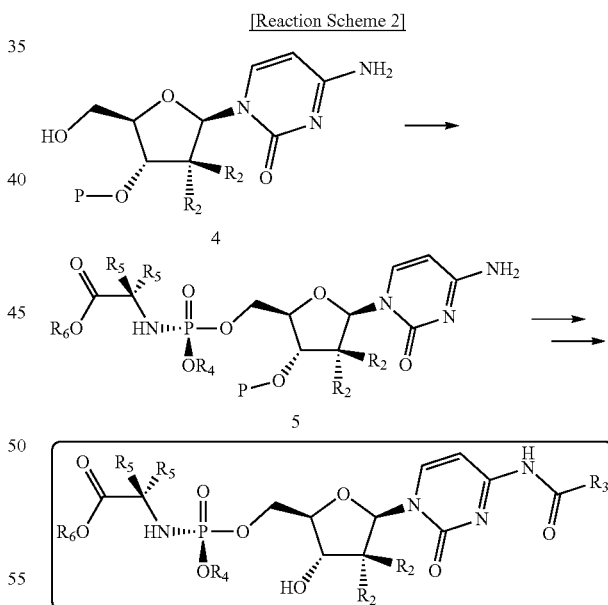

Preferably, the above reaction may be performed by reacting the compound 4 with t-BuMgCl in a THF solvent to synthesize a phosphoamidite compound 5, which is then reacted with a carbonyl halide containing a substituent $R_3$ suitable for the desired compound, followed by a deprotection reaction. Preferably, the deprotection reaction may be performed using a tetrabutylammonium fluoride (TBAF) solution at 0° C. to room temperature for 0.5 to 1 hour.

Composition Containing Nucleoside or Nucleotide Derivative Compound, Use Thereof and Method for Prevention or Treatment Using Same The present disclosure provides a pharmaceutical composition for preventing or treating diseases associated with viral infection, comprising a compound of the following Chemical Formula 1, a racemate thereof, a stereoisomer thereof, or a pharmaceutically acceptable salt thereof as an active ingredient.

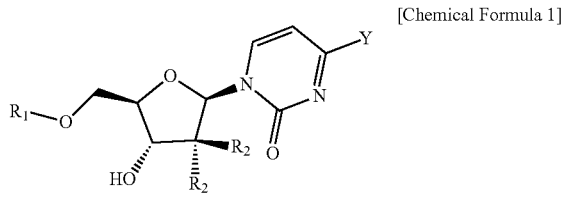

[Chemical Formula 1]

in the Chemical Formula 1, substituents are as defined above.

The compound of the Chemical Formula 1, the racemate, stereoisomer or pharmaceutically acceptable salt thereof according to the present disclosure can exhibit antiviral activity.

Therefore, the pharmaceutical composition comprising the compound of Chemical Formula 1 of the present disclosure, or the racemate, stereoisomer or pharmaceutically acceptable salt thereof as an active ingredient exhibits universal antiviral activity, and thus may be usefully used for preventing or treating diseases associated with viral infection.

Specifically, the pharmaceutical composition of the present disclosure may be usefully used for preventing or treating diseases associated with viral infection.

The viral diseases may be diseases caused by HIV, HBV, HCV, influenza, picorna, flavi, alpha, phlebovirus, ebola or corona virus, without being limited thereto.

The term "prevention" as used herein refers to any act to delay or inhibit occurrence, spread or recurrence of virus-associated diseases by administration of the composition of the present disclosure, and the term "treatment" as used herein refers to any act to improve or change the symptoms of the above diseases for the better by administration of the composition of the present disclosure.

The pharmaceutical composition according to the present disclosure may contain 0.1 to 75% by weight, more preferably 1 to 50% by weight of a compound represented by Chemical Formula 1, a racemate thereof, a stereoisomer thereof, or a pharmaceutically acceptable salt thereof as an active ingredient, based on the total weight of the composition.

In addition, the pharmaceutical composition of the present disclosure may further include a pharmaceutically acceptable carrier, diluent or excipient, and can be used in the various forms such as oral dosage forms of powders, granules, tablets, capsules, suspensions, emulsions, syrups, aerosols and injections of a sterile injectable solution formulated by the conventional method to serve the purpose of each in accordance, can be administered through various routes including oral administration or intravenous, intraperitoneal, subcutaneous, rectal and topical administration. The examples of suitable carrier, excipient, or diluent which can be included in this composition may be lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxy benzoate, propyl hydroxy benzoate, talc, magnesium stearate and mineral oil. Further, the composition of the present disclosure may further comprise fillers, anti-coagulants, lubricants, humectants, fragrances, emulsifiers, preservatives, etc.

The composition of the present disclosure is administrated in a pharmaceutically effective amount. As used herein, the term "pharmaceutically effective amount" refers to an amount sufficient to treat diseases at a reasonable benefit/risk ratio applicable to any medical treatment and not causing side effect. An effective dose level may be determined depending on a variety of factors comprising patient's health condition, type of diseases, severity, activity of drug, sensitivity to drug, administration method, administration time, administration route, excretion rate, the duration of treatment, combination or co-administered drugs, and other factors well known in the medical field. The pharmaceutical composition of the present disclosure may be administered as an individual therapeutic agent or in combination with other therapeutic agents, and may be administered sequentially or simultaneously with conventional therapeutic agents. The composition can be administered at single or multiple times. It important to administer the composition in the minimum possible amount sufficient to obtain the greatest therapeutic effect without side effects, in consideration of all the above-described factors, which can be easily determined by those skilled in the art.

Specifically, the effective amount of the compound in the composition of the present disclosure may vary depending on the age, sex or body weight of a patient, and the compound may be generally administered at a dose of 1 to 100 mg, and preferably, 5 to 60 mg per 1 kg of body weight, daily or every other day, or once to six times a day. However, the effective amount may vary depending on an administration route, the severity of diseases, sex, body weight or age of a patient, and therefore, the scope of the present disclosure is not limited by the dose in any way.

According to another embodiment of the present disclosure, there is provided a method for preventing or treating virus-associated diseases in a subject, comprising administering the compound represented by Chemical Formula 1, the racemate thereof, the stereoisomer thereof, or the pharmaceutically acceptable salt thereof to a subject in need thereof.

As used herein, the term "subject" refers to an animal comprising human, monkey, cow, horse, sheep, pig, chicken, turkey, quail, cat, dog, mouse, rat, rabbit, or guinea pig, which have the above virus-associated diseases or potentially has the diseases. The above diseases can be effectively prevented or treated by administrating the pharmaceutical composition of the present disclosure to the subject. The pharmaceutical composition of the present disclosure can be administered in combination with conventional therapeutic agents.

As used herein, the term "administration" means introduction of a prescribed amount of a substance into a patient in certain appropriate method, and the composition of the present disclosure can be administrated via any of the general routes as long as it can reach a target tissue. Specifically, a variety of administration modes are contemplated, including intraperitoneally, intravenously, intramuscularly, subcutaneously, intradermally, orally, topically, intranasally, intrapulmonarily and intrarectally, without being limited thereto. Also, the pharmaceutical composition of the present invention can be administered using any device capable of delivering the active ingredients to target cells. Preferable administration mode and formulation are an intravenous injection, a subcutaneous injection, an intradermal injection, an intramuscular injection, drip injection, or the like.

The pharmaceutical composition of the present disclosure may further include well-known drugs used for the prevention or treatment of known diseases in addition to the nucleoside or nucleotide derivative compound, the racemate thereof, the stereoisomer thereof, or the pharmaceutically acceptable salts thereof as an active ingredient, depending on the type of disease to be prevented or treated. For example, when used in the prevention or treatment of a viral disease, the composition may include well-known antiviral agents in addition to the nucleoside or nucleotide derivative compound, the racemate thereof, the stereoisomer thereof, or the pharmaceutically acceptable salts thereof as an active ingredient, and can be used in combination with other well-known therapy for the treatment of the diseases. Other therapy include chemotherapy, radiation therapy, hormonal therapy, bone marrow transplantation, stem cell replacement therapy, other biological therapy, immunotherapy, etc., without being limited thereto.

Advantageous Effects

The novel nucleoside or nucleotide derivative of the present disclosure has excellent antiviral and anticancer activities, and thus can be usefully used for preventing or treating viral infection-associated diseases.

DETAILED DESCRIPTION OF THE EMBODIMENTS

Hereinafter, the configuration and effects of the present disclosure will be described in more detail by way of examples. These examples are for illustrative purposes only and the scope of the present disclosure is not limited thereby.

Preparation Example 1: Preparation of 4-amino-1-((2R,4R,5R)-3,3-difluoro-4-(trimethylsilyloxy)-5-((trimethylsilyloxy)methyl)tetrahydrofuran-2-yl)pyrimidine-2(1H)-one (I-A)

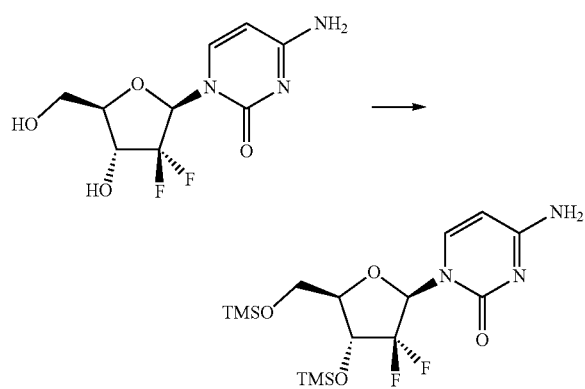

4-Amino-1-((2R,4R,5R)-3,3-difluoro-4-hydroxy-5-(hydroxymethyl)tetrahydrofuran-2-yl)pyrimidine-2(1H)-one-hydrochloride (600 mg, 2.002 mmol) was dissolved in pyridine (10 ml), and then TMSCl (0.76 ml, 6.006 mmol) was added thereto. The mixture was stirred at 55° C. to 60° C. for 17 hours. The reaction solution was diluted with EtOAc and then washed with saturated aqueous $CuSO_4$ solution for 5 times. The organic layer was dried over $Na_2SO_4$ and concentrated under reduced pressure to afford the desired product(600 mg) as a white solid.

LC-MS (ESI, m/z)=407.8(M+H$^+$)

Preparation Example 2: Preparation of 4-amino-1-((2R,3R,4R,5R)-3-fluoro-4-((trimethylsilyl)oxy)-5-(((trimethylsilyl)oxy)methyl)tetrahydrofuran-2-yl)pyrimidine-2(1H)-one (I-B)

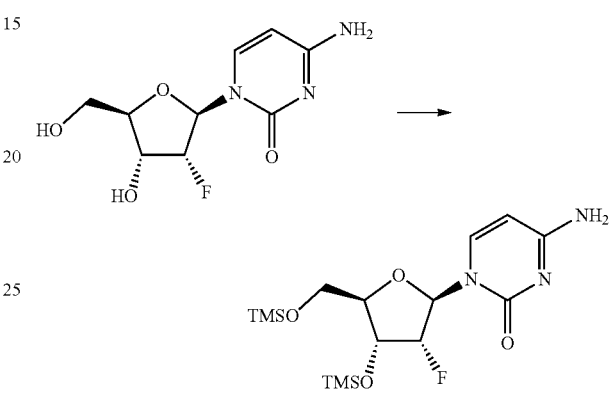

4-Amino-1-((2R,3R,4R,5R)-3-fluoro-4-hydroxy-5-(hydroxymethyl)tetrahydrofuran-2-yl)pyrimidin-2(1H)-one (1 g, 4.078 mmol) was dissolved in pyridine (10 ml), and then TMSCl (1.54 ml, 12.234 mmol) was added thereto. The mixture was stirred at 70° C. for 6 hours. The reaction solution was diluted with EtOAc and then washed with saturated aqueous $CuSO_4$ solution for 5 times. The organic layer was dried over $Na_2SO_4$ and concentrated under reduced pressure to afford the desired product(1.57 g) as a white solid.

LC-MS (ESI, m/z)=390.1(M+H$^+$)

Example 1: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide Step 1: 4-Amino-1-((2R,4R,5R)-3,3-difluoro-4-hydroxy-5-(hydroxymethyl)tetrahydrofuran-2-yl)pyrimidine-2(1H)-one-hydrochloride (1 g, 3.337 mmol) was dissolved in pyridine (16.7 ml), and then TMSCl (1.4 ml, 11.012 mmol) was added thereto. The mixture was stirred at 55° C. to 60° C. for 3.5 hours, and then nicotinoyl chloride hydrochloride (720 mg, 4.044 mmol) was added and stirred at the same temperature for 7 hours. The reaction solution was diluted with EtOAc and then washed with saturated aqueous $CuSO_4$ solution for 5 times. The organic layer was dried over $Na_2SO_4$ and concentrated under reduced pressure to afford the product(1.67 g) as a white solid.

LC-MS (ESI, m/z)=513.0(M+H$^+$)

Step 2: The compound (1.65 g, 3.219 mmol) obtained from step 1 was dissolved in DCM (6 ml), and then 4 M HCl in dioxane (8 ml) was slowly added at 0° C. After stirring at room temperature for 1 hour, the reaction solution was concentrated under reduced pressure. The residue was diluted with purified water, and 2N NaOH aqueous solution was added to adjust the pH to 6-7. The precipitated solid was filtered and dried to afford the desired product(1.08 g) as a white solid.

LC-MS (ESI, m/z)=369.0(M+H$^+$)

Example 2: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide Picolinoyl chloride hydrochloride (141.5 mg, 0.674 mmol) and I-A (260 mg, 0.683 mmol) were reacted in a similar manner as described in Example 1 to afford the desired product(71.5 mg) as a white solid.

LC-MS (ESI, m/z)=368.2(M+H$^+$)

Example 3: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-6-fluoronicotinamide 6-Fluoronicotinoylchloride (133 mg, 0.834 mmol) and I-A (200 mg, 0.490 mmol) were reacted in a similar manner as described in Example 1 to afford the desired product(38.6 mg) as a white solid.

LC-MS (ESI, m/z)=386.2(M+H$^+$)

Example 4: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylnicotinamide 6-Methylnicotinoylchloride (133 mg, 0.834 mmol) and I-A (100 mg, 0.245 mmol) were reacted in a similar manner as described in Example 1 to afford the desired product(32 mg) as a white solid.

LC-MS (ESI, m/z)=382.3(M+H$^+$)

Example 5: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)pyridazine-3-carboxamide Pyridazine-3-carbonyl chloride (210 mg, 1.472 mmol) and I-A (500 mg, 1.226 mmol) were reacted in a similar manner as described in Example 1 to afford the desired product(54.4 mg) as a white solid.

LC-MS (ESI, m/z)=369.2(M+H$^+$)

Example 6: Preparation of N-(1-((2R,4R,5R)-3,3-difluoro-4-hydroxy-5-(hydroxymethyl)tetrahydrofuran-2-yl)-4-(2-oxoimidazolidin-1-yl)pyrimidin-2(1H)-one Step 1: I-A (200 mg, 0.49 mmol) was dissolved in chloroform (5 ml). 2-chloroethylisocyanate(0.04 ml, 0.49 mmol) was added thereto, and the mixture was stirred at room temperature for 3 hours. The reaction mixture was concentrated under reduced pressure and the next reaction was carried out without purification.

Step 2: Compound obtained from step 1 was dissolved in THF (2.5 ml), 60% NaH (37 mg, 1.47 mmol) was added thereto at −20° C. The reaction temperature was gradually raised and the mixture was stirred at room temperature for 18 hours. Ice was added to the reaction mixture, stirred for 5 minutes, then diluted with EtOAc. The organic layer was dried over Na$_2$SO$_4$ and concentrated under reduced pressure.

The residue was diluted with MeOH, to which DCM was added and the precipitated solid was filtered and dried to afford the desired product(96.1 mg) as a white solid.

LC-MS (ESI, m/z)=332.2 (M+H$^+$)

Example 7: Preparation of N-(1-((2R,4R,5R)-3,3-difluoro-4-hydroxy-5-(hydroxymethyl)tetrahydrofuran-2-yl)-4-(2-oxopyrrolidin-1-yl)pyrimidin-2(1H)-one Step 1: Picolinoyl 4-bromobutyrylchloride (0.4 ml, 3.434 mmol) and TEA (1.2 ml, 8.587 mmol) were slowly added to I-A (162 mg, 0.397 mmol) dissolved in DCM (8.5 ml) at −50° C. The reaction solution was stirred at 10° C. for 24 hours, then diluted with DCM and washed with purified water. The organic layer was dried over Na$_2$SO$_4$, and concentrated under reduced pressure to afford the intermediate(800 mg), and the next reaction was carried out without purification.

Step 2: Compound (800 mg, 1.437 mmol) obtained from step 1 was reacted in a similar manner as described in Example 1 Step 2 to afford the desired product(303.2 mg) as a white solid.

LC-MS (ESI, m/z)=331.2(M+H$^+$)

Example 8: Preparation of N-(1-((2R,4R,5R)-3,3-difluoro-4-hydroxy-5-(hydroxymethyl)tetrahydrofuran-2-yl)-4-(3-methyl-2-oxoimidazolidin-1-yl)pyrimidin-2(1H)-one Step 1: (2R,3R,5R)-5-(4-Amino-2-oxopyrimidine-1(2H)-yl)-4,4-difluoro-2-((3-fluorobenzoyloxy)methyl)tetrahydrofuran-3-yl 3-fluorobenzoate (200 mg, 0.394 mmol) was dissolved in DCM(4 ml), and then pyridine(0.05 ml, 0.591 mmol) and phenyl chloroformate(0.06 ml, 0.472 mmol) were added thereto. After stirring at room temperature for 1 hour, the reaction solution was concentrated under reduced pressure. The residue was dissolved in pyridine (4 ml), and then 2-chloro-N-methylethanamine hydrochloride (256 mg, 1.97 mmol) was added and stirred at 50° C. for 8 hours. The reaction solution was diluted with EtOAc and then washed with saturated aqueous CuSO$_4$ solution for 5 times. The organic layer was dried over Na$_2$SO$_4$ and concentrated under reduced pressure to afford the product(170 mg) as a white solid.

LC-MS (ESI, m/z)=626.9(M+H$^+$)

Step 2: Compound (170 mg, 0.288 mmol) obtained from step 1 was dissolved in MeOH (1 ml), 7 N NH$_3$ in MeOH (2 ml) was added thereto. After stirring at room temperature for 18 hours, the reaction solution was concentrated under reduced pressure. The residue was purified by column chromatography to afford the desired product(64.3 mg) as a white solid.

LC-MS (ESI, m/z)=346.2 (M+H$^+$)

Example 9: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-5-fluoropicolinamide 6-fluoropicolinic acid (300 mg, 2.126 mmol) was dissolved in DCM (4.25 ml), DMF (16.5 μl, 0.213 mmol) and oxalyl chloride (0.27 ml, 3.189 mmol) were added slowly at 0° C. The reaction solution was stirred at room temperature for 22 hours and then concentrated under reduced pressure. The residue was washed with ether and dried to afford the intermediate(339 mg) as an apricot solid. The obtained 6-fluoropicolinoyl chloride (88 mg, 0.552 mmol) and DIPEA (0.48 ml, 2.76 mmol) were added slowly to I-A (150 mg, 0.368 mmol) dissolved in DCM (1.2 ml) at −78° C. The reaction solution was stirred at room temperature for 18 hours, then diluted with DCM, and washed with purified water. The organic layer was dried over $Na_2SO_4$, concentrated under reduced pressure and then purified by column chromatography to afford the desired product(36.7 mg) as a white solid.

LC-MS (ESI, m/z)=386.8(M+H$^+$)

Example 10: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methylpicolinamide 5-Methylpicolinic acid (200 mg, 1.458 mmol) was reacted with oxalyl chloride (0.38 ml, 4.374 mmol), and the obtained 5-methylpicolinoyl chloride (119 mg, 0.766 mmol) and I-A (260 mg, 0.683 mmol) were reacted in a similar manner as described in Example 8 to afford the desired product(67.5 mg) as a white solid.

LC-MS (ESI, m/z)=382.8(M+H$^+$)

Example 11: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide 2-Methyl-6-(trifluoromethyl)nicotinic acid (205 mg, 1.000 mmol) was reacted with oxalyl chloride (0.36 ml, 3.000 mmol), and the obtained 2-methyl-6-(trifluoromethyl)nicotinoyl chloride (164.7 mg, 0.737 mmol) and I-A (200 mg, 0.491 mmol) were reacted in a similar manner as described in Example 8 to afford the desired product(75 mg) as a white solid.

LC-MS (ESI, m/z)=450.6(M+H$^+$)

Example 12: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-3-methylpicolinamide Step 1: 3-Methylpicolinic acid (300 mg, 2.188 mmol) was reacted with oxalyl chloride (0.56 ml, 6.563 mmol), and the obtained 3-methylpicolinoyl chloride (86 mg, 0.552 mmol) and I-A (150 mg, 0.368 mmol) were reacted in a similar manner as described in Example 8 to afford the product(80 mg) as a yellow liquid.

LC-MS (ESI, m/z)=455.1(M+H$^+$)

Step 2: Compound (80 mg, 0.165 mmol) obtained from step 1 was reacted in a similar manner as described in Example 1 Step 2 to afford the desired product(44 mg) as a white solid.

LC-MS (ESI, m/z)=383.0(M+H$^+$)

Example 13: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylpicolinamide 6-Methylpicolinic acid (300 mg, 2.188 mmol) was reacted with oxalyl chloride (0.56 ml, 6.563 mmol), and the obtained 6-methylpicolinoyl chloride (68.7 mg, 0.442 mmol) and I-A (150 mg, 0.368 mmol) were reacted in a similar manner as described in Example 8 to afford the desired product(14.4 mg) as a white solid.

LC-MS (ESI, m/z)=383.0(M+H$^+$)

Example 14: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-6-(trifluoromethyl)nicotinamide Step 1: 6-(Trifluoromethyl)nicotinic acid (150 mg, 0.784 mmol) was reacted with oxalyl chloride (0.13 ml, 1.569 mmol), and the obtained 6-(trifluoromethyl)nicotinoyl chloride (62 mg, 0.294 mmol) and I-A(100 mg, 0.245 mmol) were reacted in a similar manner as described in Example 9 to afford the product(108 mg) as an apricot solid.

LC-MS (ESI, m/z)=581.1 (M+H$^+$)

Step 2: Compound (108 mg, 0.185 mmol) obtained from step 1 was reacted in a similar manner as described in Example 1 Step 2 afford the desired product(19.8 mg) a white solid.

LC-MS (ESI, m/z)=437.0(M+H$^+$)

Example 15: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-1-methyl-1H-pyrazole-4-carboxamide Step 1: 1-Methyl-1H-pyrazole-4-carboxylic acid (300 mg, 2.380 mmol) was reacted with oxalyl chloride (0.4 ml, 4.720 mmol), and the obtained 1-methyl-1H-pyrazole-4-carbonyl chloride (85 mg, 0.588 mmol) and I-A (200 mg, 0.490 mmol) were reacted in a similar manner as described in Example 9 to afford the product(148 mg) as an apricot solid.

LC-MS (ESI, m/z)=516.1 (M+H$^+$)

Step 2: Compound (148 mg, 0.287 mmol) obtained from step 1 was reacted in a similar manner as described in Example 1 Step 2 to afford the desired product(18.2 mg) as a white solid.

LC-MS (ESI, m/z)=372.1(M+H$^+$)

Example 16: Preparation of isopropyl ((S)-(((2R, 3R,5R)-4,4-difluoro-3-hydroxy-5-(4-(nicotinamido)-2-oxopyrimidine-1(2H)-yl)tetrahydrofuran-2-yl) methoxy)(phenoxy)phosphoryl)-L-alaninate Step 1: 4-Amino-1-((2R,4R,5R)-4-((tert-butyldimethylsilyl)oxy)-3,3-difluoro-5-(hydroxymethyl)tetrahydrofuran-2-yl)pyrimidin-2(1H)-one (365 mg, 0.967 mmol) was dissolved in THF(10 ml) and cooled to 0° C. 0.85 ml of t-BuMgCl (1.7 M in THF) was slowly added and stirred for 15 minutes. Isopropyl ((R)-(perfluorophenoxy)(phenoxy) phosphoryl)-L-alaninate was dissolved in a small amount of THF and then slowly added. After slowly raising the temperature to room temperature, the reaction mixture was stirred at room temperature for 22 hours. The reaction solution was concentrated and then purified by column chromatography to afford the product(442 mg) as a white solid.

LC-MS (ESI, m/z)=647.2 (M+H$^+$)

Step 2: Compound (442 mg, 0.683 mmol) obtained from step 1 was reacted in a similar manner as described in Example 1 Step 1 to afford the product(497 mg) as a white solid.

LC-MS (ESI, m/z)=752.2(M+H$^+$)

Step 3: Compound (442 mg, 0.683 mmol) obtained from step 2 was dissolved in THF (0.5 ml) and cooled to 0° C. 0.16 ml of TBAF 1M in THF was slowly added, and then stirred at room temperature for 30 minutes. The reaction solution was concentrated under reduced pressure and then purified by column chromatography to afford the desired product(52 mg) as a white solid.

LC-MS (ESI, m/z)=638.1(M+H$^+$)

Example 17: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-6-phenylpicolinamide Step 1: 6-Phenylpicolinic acid (250 mg, 1.254 mmol) was reacted with oxalyl chloride (0.27 ml, 3.189 mmol), and the obtained 6-phenylpicolinoyl chloride (159.9 mg, 0.735 mmol) and I-A (200 mg, 0.49 mmol) were reacted in a similar manner as described in Example 9 to afford the intermediate as a yellow liquid without purification, and the next reaction was carried out.

LC-MS (ESI, m/z)=589.1(M+H$^+$)

Step 2: Compound (0.49 mmol) obtained from step 1 was reacted in a similar manner as described in Example 1 Step 2 to afford the desired product(123 mg) as a white solid.

LC-MS (ESI, m/z)=445.0(M+H$^+$)

Example 18: Preparation of 1-((2R,4R,5R)-3,3-difluoro-4-hydroxy-5-(hydroxymethyl)tetrahydrofuran-2-yl)-4-(3-methyl-2-oxopyrrolidin-1-yl)pyrimidin-2(1H)-one Step 1: 3-Methyldihydrofuran-2(3H)-one (1 g, 9.988 mmol) was reacted with hydrogen bromide solution (33 wt. % in acetic acid, 9.98 ml, 30.266 mmol) and thionyl chloride(6 ml, 50.432 mmol), and the obtained 4-bromo-2-methylbutanoyl chloride (0.12 ml, 0.919 mmol) and I-A (250 mg, 0.513 mmol) was carried out in a similar manner as described in Example 9 to afford the product(349 mg) as an orange solid.

LC-MS (ESI, m/z)=516.1 (M+H$^+$)

Step 2: Compound (300 mg, 0.581 mmol) obtained from step 1 was dissolved in DMF (0.6 ml), TEA (0.2 ml, 1.402 mmol) was added thereto and reacted in a microwave reactor at 200° C. for 1 hour. The reaction solution was diluted with EtOAc and then washed with purified water. The organic layer was dried over Na$_2$SO$_4$ and concentrated under reduced pressure to afford the desired product(210 mg) as a yellow solid.

LC-MS (ESI, m/z)=490.1(M+H$^+$)

Example 19: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-5-nitropicolinamide Step 1: 5-Nitropicolinic acid (300 mg, 1.785 mmol) was reacted with oxalyl chloride (0.46 ml, 5.353 mmol), and the obtained 5-nitropicolinoyl chloride (98.6 mg, 0.442 mmol) and I-A (150 mg, 0.368 mmol) were reacted in a similar manner as described in Example 8 to afford the product(100 mg) as an yellow solid.

LC-MS (ESI, m/z)=558.0 (M+H$^+$)

Step 2: Compound (100 mg, 0.179 mmol) obtained from step 1 was reacted in a similar manner as described in Example 1 Step 2 to afford the desired product(59 mg) as a yellow solid.

LC-MS (ESI, m/z)=414.0(M+H$^+$)

Example 20: Preparation of 5-amino-N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide-hydrochloride The compound (110 mg, 0.197 mmol) obtained from step 1 of Example 19 was reacted with 10% Pd/C (55 mg) under hydrogen gas, and the obtained compound (90 mg, 0.197 mmol) was reacted in a similar manner as described in Example 1 Step 2 to afford the desired product(82 mg) as a yellow solid.

LC-MS (ESI, m/z)=384.1 (M+H$^+$)

Example 21: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methoxypicolinamide Step 1: 5-Methoxypicolinic acid (200 mg, 1.305 mmol) was reacted with oxalyl chloride (0.28 ml, 3.264 mmol), and the obtained 5-methoxypicolinoyl chloride (126 mg, 0.735 mmol) and I-A (200 mg, 0.49 mmol) were reacted in a similar manner as described in Example 8 to afford the product(110 mg) as a white solid.

LC-MS (ESI, m/z)=543.2 (M+H$^+$)

Step 2: Compound (110 mg, 0.202 mmol) obtained from step 1 was reacted in a similar manner as described in Example 1 Step 2 to afford the desired product(35 mg) as a white solid.

LC-MS (ESI, m/z)=399.0(M+H$^+$)

Example 22: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methoxynicotinamide Step 1: 6-Methoxynicotinic acid (200 mg, 1.305 mmol) was reacted with oxalyl chloride (0.22 ml, 2.611 mmol), and the obtained 6-methoxynicotinoyl chloride (168 mg, 0.980 mmol) and 4-amino-1-((2R,4R,5R)-3,3-difluoro-4-hydroxy-5-(hydroxymethyl)tetrahydrofuran-2-yl)pyrimidine-2(1H)-one-hydrochloride (200 mg, 0.668 mmol) were reacted in a similar manner as described in Example 1 to afford the product(106 mg) as a white solid.

LC-MS (ESI, m/z)=543.1 (M+H$^+$)

Step 2: Compound (106 mg, 0.195 mmol) obtained from step 1 was reacted in a similar manner as described in Example 1 Step 2 to afford the desired product(71.8 mg) as a white solid.

LC-MS (ESI, m/z)=399.1(M+H$^+$)

Example 23: Preparation of 6-chloro-N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide Step 1: 6-Chloronicotinoyl chloride (117 mg, 0.668 mmol) and 4-amino-1-((2R,4R,5R)-3,3-difluoro-4-hydroxy-5-(hydroxymethyl)tetrahydrofuran-2-yl)pyrimidine-2(1H)-one-hydrochloride (200 mg, 0.668 mmol) were reacted in a similar manner as described in Example 1 to afford the product(95 mg) as a white solid.

LC-MS (ESI, m/z)=547.1 (M+H$^+$)

Step 2: Compound (95 mg, 0.173 mmol) obtained from step 1 was reacted in a similar manner as described in Example 1 Step 2 to afford the desired product(30.4 mg) as a white solid.

LC-MS (ESI, m/z)=403.0(M+H$^+$)

Example 24: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methylpyrimidin-4-carboxamide Step 1: 2-Methylpyrimidine-4-carboxylic acid (200 mg, 1.448 mmol) was reacted with oxalyl chloride (0.24 ml, 2.896 mmol), and the obtained 2-methylpyrimidine-4-carbonyl chloride (104 mg, 0.668 mmol) and 4-amino-1-((2R,4R,5R)-3,3-difluoro-4-hydroxy-5-(hydroxymethyl)tetrahydrofuran-2-yl)pyrimidine-2(1H)-one-hydrochloride (200 mg, 0.668 mmol) were reacted in a similar manner as described in Example 1 to afford the product(246 mg) as a white solid.

LC-MS (ESI, m/z)=527.1 (M+H$^+$)

Step 2: Compound (246 mg, 0.466 mmol) obtained from step 1 was reacted in a similar manner as described in Example 1 Step 2 to afford the desired product(83 mg) as a white solid.

LC-MS (ESI, m/z)=384.1(M+H$^+$)

Example 25: Preparation of N-(1-((2R,4R,5R)-3,3-difluoro-4-hydroxy-5-(hydroxymethyl)tetrahydrofuran-2-yl)-2-oxo-1,2-dihydropyrimidin-4-yl)-5-phenylpicolinamide Step 1: 5-Phenylpicolinic acid (300 mg, 1.505 mmol) was reacted with oxalyl chloride (0.25 ml, 3.011 mmol), and the obtained 5-phenylpicolinoyl chloride (138 mg, 0.637 mmol) and I-A (200 mg, 0.490 mmol) were reacted in a similar manner as described in Example 9 to afford the product(190 mg) as an apricot solid.

LC-MS (ESI, m/z)=589.2 (M+H$^+$)

Step 2: Compound (190 mg, 0.322 mmol) obtained from step 1 was reacted in a similar manner as described in Example 1 Step 2 to afford the desired product(49.7 mg) as a white solid.

LC-MS (ESI, m/z)=445.1(M+H$^+$)

Example 26: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide Step 1: Nicotinoyl chloride HCl (158.6 mg, 0.891 mmol) and I-B (315.5 mg, 0.81 mmol) were reacted in a similar manner as described in Example 9 to afford the product(130 mg) as a white solid.

LC-MS (ESI, m/z)=493.1 (M+H$^+$)

Step 2: Compound (130 mg, 0.262 mmol) obtained from step 1 was reacted in a similar manner as described in Example 1 Step 2 to afford the desired product(60 mg) as a white solid.

LC-MS (ESI, m/z)=351.0(M+H$^+$)

Example 27: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-phenylpicolinamide Step 1: 4-Amino-1-((2R,3R,4R,5R)-3-fluoro-4-hydroxy-5-(hydroxymethyl)tetrahydrofuran-2-yl)pyrimidine-2(1H)-one (200 mg, 0.407 mmol) was dissolved in pyridine (2 ml), and then TMSCl (0.3 ml, 1.223 mmol) was added thereto. The mixture was stirred at 55° C. to 60° C. for 6 hours, then cooled to 5° C., to which 6-phenylpicolinoyl chloride (177 mg, 0.407 mmol) was added and stirred at the same temperature for 1 hour. The reaction solution was diluted with EtOAc and then washed with saturated aqueous CuSO$_4$ solution for 5 times. The organic layer was dried over Na$_2$SO$_4$ and concentrated under reduced pressure to afford the product(272 mg) as a white solid.

LC-MS (ESI, m/z)=571.2 (M+H$^+$)

Step 2: Compound (272 mg, 0.477 mmol) obtained from step 1 was reacted in a similar manner as described in Example 1 Step 2 to afford the desired product(134 mg) as a white solid.

LC-MS (ESI, m/z)=427.1(M+H$^+$)

Example 28: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-phenylpicolinamide Step 1: 5-Phenylpicolinic acid (300 mg, 1.505 mmol) was reacted with oxalyl chloride (0.25 ml, 3.011 mmol), and the obtained 5-phenylpicolinoyl chloride (111 mg, 0.513 mmol) and I-B (200 mg, 0.513 mmol) were reacted in a similar manner as described in Example 9 to afford the product(125 mg) as an apricot solid.

LC-MS (ESI, m/z)=571.2 (M+H$^+$)

Step 2: Compound (125 mg, 0.219 mmol) obtained from step 1 was reacted in a similar manner as described in Example 1 Step 2 to afford the desired product(69.5 mg) as a white solid.

LC-MS (ESI, m/z)=427.1(M+H$^+$)

Example 29: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methylpyrimidin-4-carboxamide Step 1: 2-Methylpyrimidine-4-carboxylic acid (200 mg, 1.448 mmol) was reacted with oxalyl chloride (0.24 ml, 2.896 mmol), and the obtained 2-methylpyrimidine-4-carbonyl chloride (104 mg, 0.668 mmol) and 4-amino-1-((2R,3R,4R,5R)-3-fluoro-4-hydroxy-5-(hydroxymethyl)tetrahydrofuran-2-yl)pyrimidin-2(1H)-one (200 mg, 0.816 mmol) were reacted in a similar manner as described in Example 27 to afford the product(320 mg) as a white solid.

LC-MS (ESI, m/z)=510.1 (M+H$^+$)

Step 2: Compound (320 mg, 0.627 mmol) obtained from step 1 was reacted in a similar manner as described in Example 1 Step 2 to afford the desired product(174.5 mg) as a white solid.

LC-MS (ESI, m/z)=366.1(M+H$^+$)

Example 30: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-nitropicolinamide Step 1: 5-Nitropicolinic acid (300 mg, 1.785 mmol) was reacted with oxalyl chloride(0.46 ml, 5.353 mmol), and the obtained 5-nitropicolinoyl chloride (143 mg, 0.4770 mmol) and I-B (300 mg, 0.770 mmol) were reacted in a similar manner as described in Example 9 to afford the product(213 mg) as a yellow solid.

LC-MS (ESI, m/z)=540.1 (M+H$^+$)

Step 2: Compound (213 mg, 0.394 mmol) obtained from step 1 was reacted in a similar manner as described in Example 1 Step 2 to afford the desired product(64.6 mg) as a white solid.
LC-MS (ESI, m/z)=396.0(M+H⁺)

Example 31: Preparation of 5-amino-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide The compound (58 mg, 0.146 mmol) obtained from Example 30 Step 2 was reacted with 10% Pd/C (55 mg) under hydrogen gas, filtered through Celite pad, and concentrated under reduced pressure to afford the desired product(32.8 mg) as a white solid.
LC-MS (ESI, m/z)=366.1 (M+H⁺)

Example 32: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylnicotinamide Step 1: 6-Methylnicotinic acid (400 mg, 2.916 mmol) was reacted with oxalyl chloride (0.5 ml, 5.833 mmol), and the obtained 6-methylnicotinoyl chloride (126 mg, 0.816 mmol) and 4-amino-1-((2R,3R,4R,5R)-3-fluoro-4-hydroxy-5-(hydroxymethyl)tetrahydrofuran-2-yl)pyrimidin-2(1H)-one (200 mg, 0.816 mmol) were reacted in a similar manner as described in Example 27 to afford the product(159 mg) as a white solid.
LC-MS (ESI, m/z)=509.2 (M+H⁺)
Step 2: Compound (159 mg, 0.312 mmol) obtained from step 1 was reacted in a similar manner as described in Example 1 Step 2 to afford the desired product(103.9 mg) as a white solid.
LC-MS (ESI, m/z)=365.1(M+H⁺)

Example 33: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)pyridazine-3-carboxamide Step 1: Pyridazine-3-carboxylic acid (415 mg, 3.344 mmol) was reacted with oxalyl chloride (0.85 ml, 10.032 mmol), and the obtained pyridazine-3-carbonyl chloride (586 mg, 3.303 mmol) and 4-amino-1-((2R,3R,4R,5R)-3-fluoro-4-hydroxy-5-(hydroxymethyl)tetrahydrofuran-2-yl)pyrimidin-2(1H)-one (700 mg, 2.753 mmol) were reacted in a similar manner as described in Example 27 to afford the product(729 mg) as a yellow solid.
LC-MS (ESI, m/z)=496.1 (M+H⁺)
Step 2: Compound (729 mg, 1.470 mmol) obtained from step 1 was reacted in a similar manner as described in Example 1 Step 2, and the precipitated solid was filtered and dried to afford the desired product(523.2 mg) as a white solid.
LC-MS (ESI, m/z)=352.1 (M+H⁺)

Example 34: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylpyrazine-2-carboxamide Step 1: 6-Methylpyrazine-2-carboxylic acid (200 mg, 1.448 mmol) was reacted with oxalyl chloride (0.24 ml, 2.896 mmol), and the obtained 6-methylpyrazine-2-carbonyl chloride (88.4 mg, 0.564 mmol) and I-B (200 mg, 0.513 mmol) were reacted in a similar manner as described in Example 9 to afford the product(115 mg) as a white solid.
LC-MS (ESI, m/z)=510.1 (M+H⁺)
Step 2: Compound (115 mg, 0.225 mmol) obtained from step 1 was reacted in a similar manner as described in Example 1 Step 2 to afford the desired product(54 mg) as a white solid.
LC-MS (ESI, m/z)=366.1 (M+H⁺)

Example 35: Preparation of 5-fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide Step 1: 5-Fluoropicolinic acid (141 mg, 1 mmol) was reacted with oxalyl chloride (0.257 ml, 3 mmol), and the obtained 5-fluoropicolinoyl chloride HCl (120.54 mg, 0.615 mmol) and I-B (200 mg, 0.513 mmol) were reacted in a similar manner as described in Example 9 to afford the product(115 mg) as a white solid.
LC-MS (ESI, m/z)=513.2 (M+H⁺)
Step 2: Compound (115 mg, 0.22 mmol) obtained from step 1 was reacted in a similar manner as described in Example 1 Step 2 to afford the desired product(48 mg) as a white solid.
LC-MS (ESI, m/z)=369.0 (M+H⁺)

Example 36: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)pyrimidine-4-carboxamide Step 1: Pyrimidine-4-carboxylic acid (200 mg, 1.611 mmol) was reacted with oxalyl chloride (0.4 ml, 4.833 mmol), and the obtained pyrimidine-4-carbonyl chloride (137.6 mg, 0.769 mmol) and I-B (200 mg, 0.513 mmol) were reacted in a similar manner as described in Example 9 to afford the product(106 mg) as a white solid.
LC-MS (ESI, m/z)=496.1 (M+H⁺)
Step 2: Compound (115 mg, 0.225 mmol) obtained from step 1 was reacted in a similar manner as described in Example 1 Step 2 to afford the desired product(54 mg) as a white solid.
LC-MS (ESI, m/z)=352.1 (M+H⁺)

Example 37: Preparation of 5-cyano-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide Step 1: 5-Cyanopicolinic acid (148 mg, 1 mmol) was reacted with oxalyl chloride (0.257 ml, 3 mmol), and the obtained 5-cyanopicolinoyl chloride HCl (125 mg, 0.615 mmol) and I-B (200 mg, 0.513 mmol) were reacted in a similar manner as described in Example 9 to afford the product(100 mg) as a yellow liquid.
LC-MS (ESI, m/z)=520.0 (M+H⁺)
Step 2: Compound (100 mg, 0.192 mmol) obtained from step 1 was reacted in a similar manner as described in Example 1 Step 2 to afford the desired product(52 mg) as a yellow solid.
LC-MS (ESI, m/z)=376.0 (M+H⁺)

Example 38: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methylpicolinamide Step 1: 5-Methylpicolinic acid (200 mg, 1.458 mmol) was reacted with oxalyl chloride (0.37 ml, 4.375 mmol), and the obtained 5-methylpicolinoyl chloride (197 mg, 1.026 mmol) and I-B (200 mg, 0.513 mmol) were reacted in a similar manner as described in Example 9 to afford the product(215 mg) as a white liquid.

LC-MS (ESI, m/z)=509.2 (M+H$^+$)

Step 2: Compound (215 mg, 0.422 mmol) obtained from step 1 was reacted in a similar manner as described in Example 1 Step 2 to afford the desired product(106.4 mg) as a white solid.

LC-MS (ESI, m/z)=365.1 (M+H$^+$)

Example 39: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methoxypicolinamide Step 1: 5-Methoxypicolinic acid (200 mg, 1.305 mmol) was reacted with oxalyl chloride (0.33 ml, 3.915 mmol), and the obtained 5-methoxypicolinoyl chloride (213 mg, 1.026 mmol) and I-B (200 mg, 0.513 mmol) were reacted in a similar manner as described in Example 9 to afford the product(139 mg) as a white liquid.

LC-MS (ESI, m/z)=525.1 (M+H$^+$)

Step 2: Compound (139 mg, 0.264 mmol) obtained from step 1 was reacted in a similar manner as described in Example 1 Step 2 to afford the desired product(57 mg) as a white solid.

LC-MS (ESI, m/z)=381.1 (M+H$^+$)

Example 40: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide Step 1: 2-Methyl-6-(trifluoromethyl)nicotinic acid (200 mg, 0.974 mmol) was reacted with oxalyl chloride (0.25 ml, 2.922 mmol), and the obtained 2-methyl-6-(trifluoromethyl) nicotinoyl chloride (329 mg, 1.572 mmol) and 4-amino-1-((2R,3R,4R,5R)-3-fluoro-4-hydroxy-5-(hydroxymethyl)tetrahydrofuran-2-yl)pyrimidin-2(1H)-one (200 mg, 0.816 mmol) were reacted in a similar manner as described in Example 27 to afford the product(98 mg) as a yellow liquid.

LC-MS (ESI, m/z)=577.1 (M+H$^+$)

Step 2: Compound (98 mg, 0.169 mmol) obtained from step 1 was reacted in a similar manner as described in Example 1 Step 2 to afford the desired product(64.8 mg) as a white solid.

LC-MS (ESI, m/z)=433.1 (M+H$^+$)

Example 41: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-(trifluoromethyl)nicotinamide Step 1: 6-(Trifluoromethyl)nicotinic acid (200 mg, 1.046 mmol) was reacted with oxalyl chloride (0.26 ml, 3.139 mmol), and the obtained 6-(trifluoromethyl)nicotinoyl chloride (189 mg, 0.769 mmol) and 4-amino-1-((2R,3R,4R,5R)-3-fluoro-4-hydroxy-5-(hydroxymethyl)tetrahydrofuran-2-yl)pyrimidin-2(1H)-one (200 mg, 0.816 mmol) were reacted in a similar manner as described in Example 27 to afford the product(202 mg) as a yellow solid.

LC-MS (ESI, m/z)=563.1 (M+H$^+$)

Step 2: Compound (202 mg, 0.359 mmol) obtained from step 1 was reacted in a similar manner as described in Example 1 Step 2 to afford the desired product(66 mg) as a white solid.

LC-MS (ESI, m/z)=419.0 (M+H$^+$)

Example 42: Preparation of 6-fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl) nicotinamide Step 1: 6-Fluoronicolinic acid (200 mg, 1.417 mmol) was reacted with oxalyl chloride (0.36 ml, 4.252 mmol), and the obtained 6-fluoronicolinoyl chloride (100.5 mg, 0.513 mmol) and I-B (200 mg, 0.513 mmol) were reacted in a similar manner as described in Example 9 to afford the product(175 mg) as a yellow solid.

LC-MS (ESI, m/z)=513.1 (M+H$^+$)

Step 2: Compound (175 mg, 0.342 mmol) obtained from step 1 was reacted in a similar manner as described in Example 1 Step 2 to afford the desired product(15 mg) as a white solid.

LC-MS (ESI, m/z)=369.0 (M+H$^+$)

Example 43: Preparation of N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methoxynicotinamide Step 1: 6-Methoxypicolinic acid (200 mg, 1.305 mmol) was reacted with oxalyl chloride (0.33 ml, 3.915 mmol), and the obtained 6-methoxypicolinoyl chloride (213 mg, 1.026 mmol) and I-B (200 mg, 0.513 mmol) were reacted in a similar manner as described in Example 9 to afford the product(125 mg) as a white solid.

LC-MS (ESI, m/z)=525.1 (M+H$^+$)

Step 2: Compound (125 mg, 0.238 mmol) obtained from step 1 was reacted in a similar manner as described in Example 1 Step 2 to afford the desired product(31.4 mg) as a white solid.

LC-MS (ESI, m/z)=381.1 (M+H$^+$)

Example 44: Preparation of isopropyl ((S)-(((2R,3R,4R,5R)-4-fluoro-3-hydroxy-5-(4-(2-methylpyrimidine-4-carboxamido)-2-oxopyridin-1(2H)-yl)tetrahydrofuran-2-yl)methoxy)(phenoxy)phosphoryl)-L-alaninate Step 1: 4-Amino-1-((2R,3R,4R,5R)-4-((tert-butyldimethylsilyl)oxy)-3-fluoro-5-(hydroxymethyl)tetrahydrofuran-2-yl)pyrimidin-2(1H)-one (395 mg, 1.10 mmol) was reacted in a similar manner as described in Example 16 Step 1 to afford the product(318 mg) as a yellow solid.

LC-MS (ESI, m/z)=629.2 (M+H$^+$)

Step 2: Compound (307 mg, 0.488 mmol) obtained from step 1 was reacted in a similar manner as described in Example 9 to afford the product(345 mg) as a yellow solid.

LC-MS (ESI, m/z)=749.2 (M+H$^+$)

Step 3: Compound (120 mg, 0.160 mmol) obtained from step 2 was dissolved in THF (0.8 ml) and cooled to −5° C. After slowly adding 0.17 ml of TBAF 1M in THF, the mixture was stirred at the same temperature for 20 minutes. Water was added to the reaction solution, diluted with EtOAc, and then washed with water for 3 times. The organic layer was dried over Na$_2$SO$_4$, concentrated under reduced pressure, and then purified by column chromatography to afford the desired product(60 mg) as a white solid.

LC-MS (ESI, m/z)=635.0 (M+H$^+$)

The above Examples are summarized by structure and name in Table 1 below.

TABLE 1

| Example | Structure | Name |
|---|---|---|
| 1 | 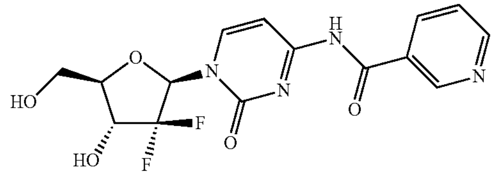 | N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide |
| 2 | 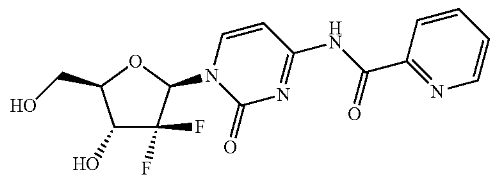 | N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide |
| 3 | 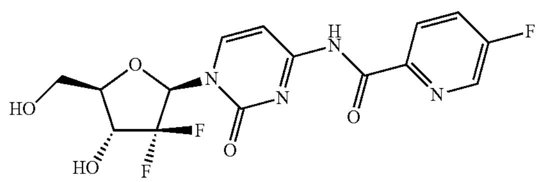 | N-(1-((2R,4R,5R)-3,3-difluoro-4-hydroxy-5-(hydroxymethyl)tetrahydrofuran-2-yl)-2-oxo-1,2-dihydropyrimidin-4-yl)-6-fluoronicotinamide |
| 4 | 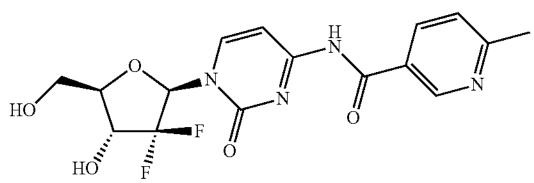 | N-(1-((2R,4R,5R)-3,3-difluoro-4-hydroxy-5-(hydroxymethyl)tetrahydrofuran-2-yl)-2-oxo-1,2-dihydropyrimidn-4-yl)-6-methylnicotinamide |
| 5 | 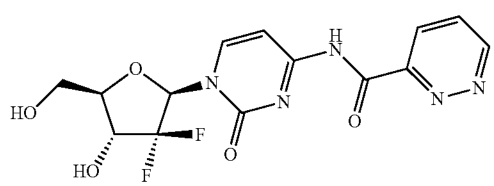 | N-(1-((2R,4R,5R)-3,3-difluoro-4-hydroxy-5-(hydroxymethyl)tetrahydrofuran-2-yl)-2-oxo-1,2-dihydropyrimidin-4-yl)pyridazine-3-carboxamide |
| 6 | 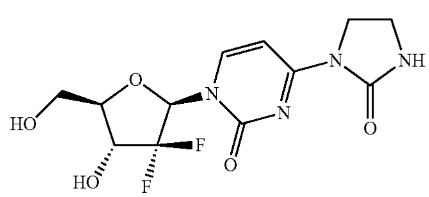 | N-(1-((2R,4R,5R)-3,3-difluoro-4-hydroxy-5-(hydroxymethyl)tetrahydrofuran-2-yl)-4-(2-oxoimidazolidin-1-yl)pyrimidin-2(1H)-one |
| 7 | 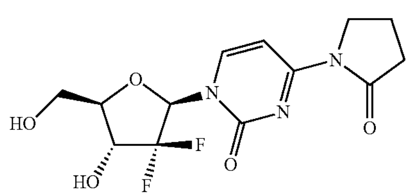 | N-(1-((2R,4R,5R)-3,3-difluoro-4-hydroxy-5-(hydroxymethyl)tetrahydrofurna-2-yl)-4-(2-oxopyrrolidin-1-yl)pyrimidin-2(1H)-one |

TABLE 1-continued

| Example | Structure | Name |
|---|---|---|
| 8 | 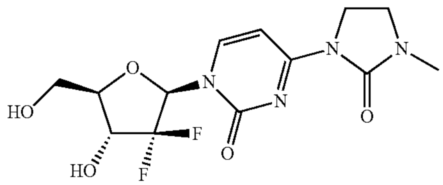 | N-(1-((2R,4R,5R)-3,3-difluoro-4-hydroxy-5-(hydroxymethyl)tetrahydrofuran-2-yl)-4-(3-methyl-2-oxoimidazolidin-1-yl)pyrimidin-2(1H)-one |
| 9 | 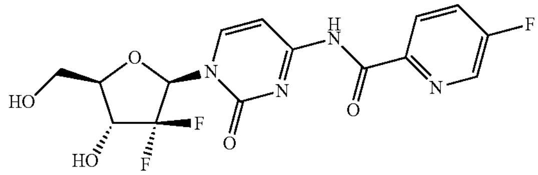 | N-(1-((2R,4R,5R)-3,3-difluoro-4-hydroxy-5-(hydroxymethyl)tetrahydrofuran-2-yl)-2-oxo-1,2-dihydropyrimidin-4-yl)-5-fluoropicolinamide |
| 10 | 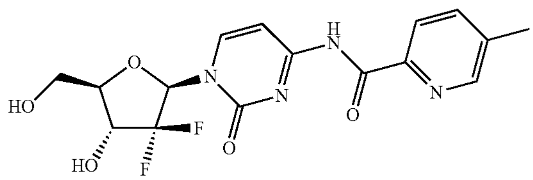 | N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methylpicolinamide |
| 11 | 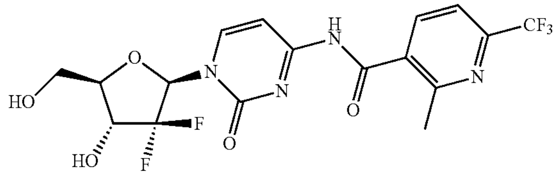 | N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide |
| 12 | 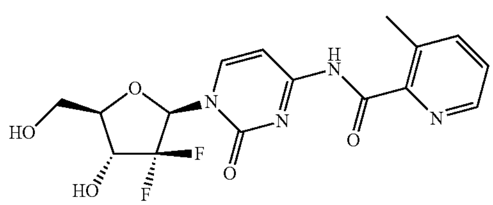 | N-(1-((2R,4R,5R)-3,3-difluoro-4-hydroxy-5-(hydroxymethyl)tetrahydrofuran-2-yl)-2-oxo-1,2-dihydropyrimmidin-4-yl)-3-methylpicolinamide |
| 13 | 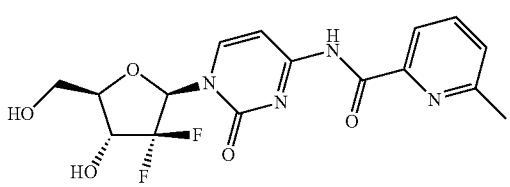 | N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylpicolinamide |
| 14 | 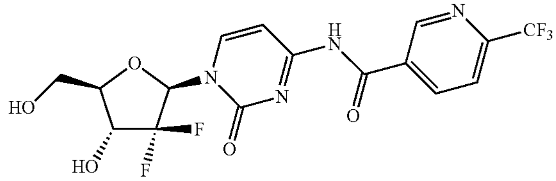 | N-(1-((2R,4R,5R)-3,3-difluoro-4-hydroxy-5-(hydroxymethyl)tetrahydrofuran-2-yl)-2-oxo-1,2-dihydropyrimidin-4-yl)-6-(trifluoromethyl)nicotinamide |
| 15 | 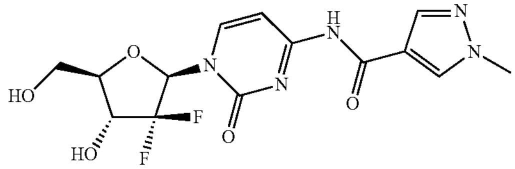 | N-(1-((2R,4R,5R)-3,3-difluoro-4-hydroxy-5-(hydroxymethyl)tetrahydrofuran-2-yl)-2-oxo-1,2-dihydropyrimidin-4-yl)-1-methyl-1H-pyrazole-4-carboxamide |

TABLE 1-continued

| Example | Structure | Name |
|---|---|---|
| 16 | 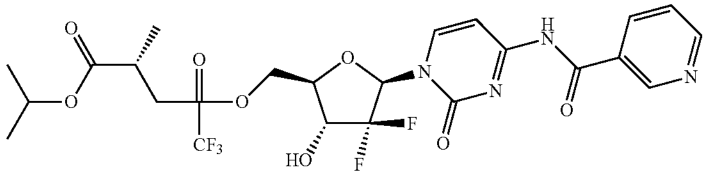 | Isopropyl ((S)-(((2R,3R,5R-4,4-difluoro-3-hydroxy-5-(4-(nicotinamido)-2-oxopyrimidine-1(2H)-yl)tetrahydrofuran-2-yl)methoxy)(phenoxy)phosphoryl)-L-alaninate |
| 17 | 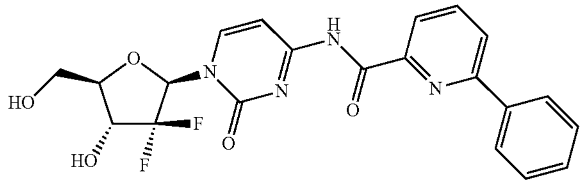 | N-(1-((2R,4R,5R)-3,3-difluoro-4-hydroxy-5-(hydroxymethyl)tetrahydrofuran-2-yl)-2-oxo-1,2-dihydropyrimidin-4-yl)-6-phenylpicolinamide |
| 18 | 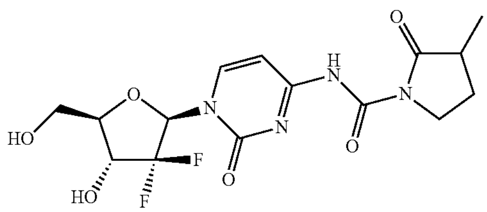 | 1-((2R,4R,5R)-3,3-difluoro-4-hydroxy-5-(hydroxymethyl)tetrahydrofuran-2-yl)-4-(3-methyl-2-oxopyrrolidin-1-yl)pyrimidin-2(1H)-one |
| 19 | 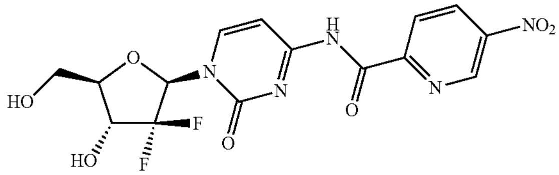 | N-(1-((2R,4R,5R)-3,3-difluoro-4-hydroxy-5-(hydroxymethyl)tetrahydrofuran-2-yl)-2-oxo-1,2-dihydropyrimidin-4-yl)-5-nitropicolinamide |
| 20 | 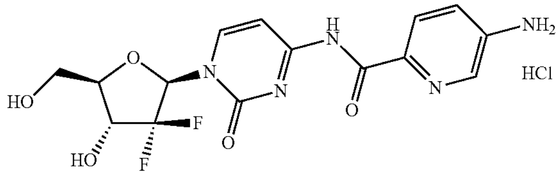 | 5-amino-N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide•hydrochloride |
| 21 | 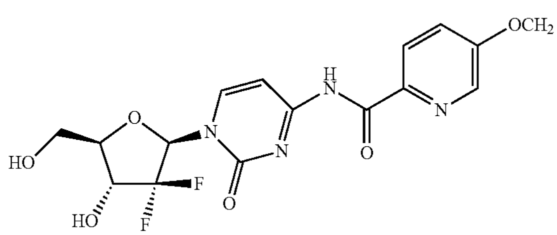 | N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methoxypicolinamide |
| 22 | 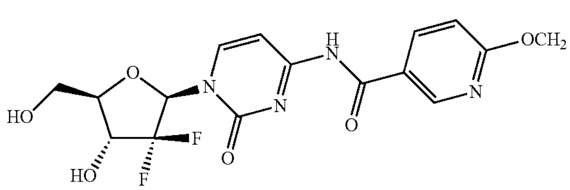 | N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methoxynicotinamide |
| 23 | 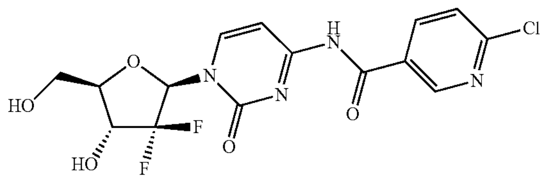 | 6-Chloro-N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide |

TABLE 1-continued

| Example | Structure | Name |
|---|---|---|
| 24 | 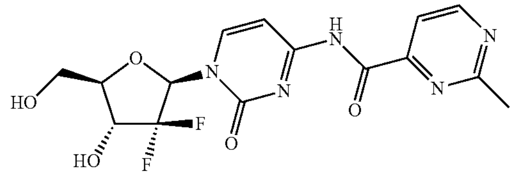 | N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methylpyrimidin-4-carboxamide |
| 25 | 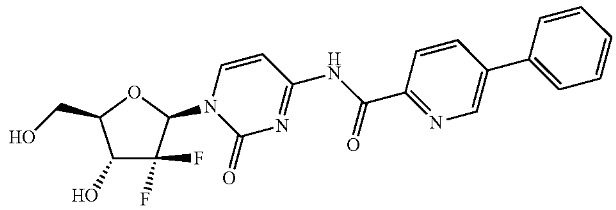 | N-(1-((2R,4R,5R)-3,3-difluoro-4-hydroxy-5-(hydroxymethyl)tetrahydrofuran-2-yl)-2-oxo-1,2-dihydropyrimidin-4-yl)-5-phenylpicolinamide |
| 26 | 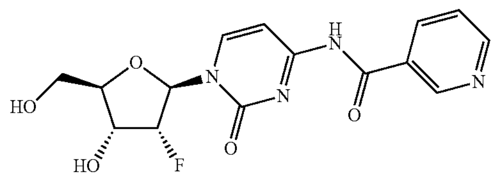 [SMILES: O=C(Nc1ccn([C@@H]2O[C@H](CO)[C@@H](O)[C@H]2F)c(=O)n1)c1cccnc1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide |
| 27 | 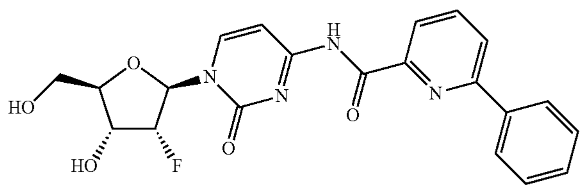 [SMILES: O=C(Nc1ccn([C@@H]2O[C@H](CO)[C@@H](O)[C@H]2F)c(=O)n1)c1cccc(-c2ccccc2)n1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-phenylpicolinamide |
| 28 | 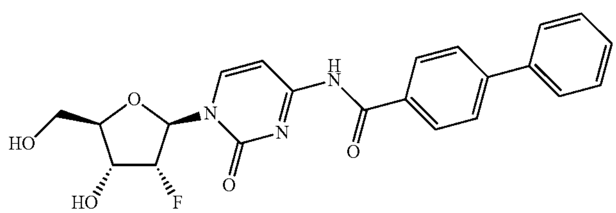 [SMILES: O=C(Nc1ccn([C@@H]2O[C@H](CO)[C@@H](O)[C@H]2F)c(=O)n1)c1ccc(-c2ccccc2)cc1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-phenylpicolinamide |
| 29 | 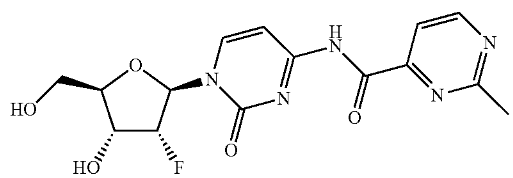 [SMILES: Cc1nccc(C(=O)Nc2ccn([C@@H]3O[C@H](CO)[C@@H](O)[C@H]3F)c(=O)n2)n1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methylpyrimidin-4-carboxamide |
| 30 | 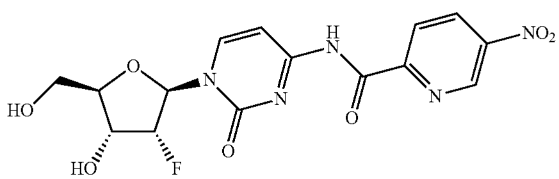 [SMILES: O=C(Nc1ccn([C@@H]2O[C@H](CO)[C@@H](O)[C@H]2F)c(=O)n1)c1ccc([N+](=O)[O-])cn1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-nitropicolinamide |
| 31 | 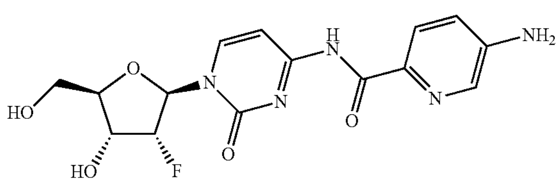 [SMILES: Nc1ccc(C(=O)Nc2ccn([C@@H]3O[C@H](CO)[C@@H](O)[C@H]3F)c(=O)n2)nc1] | 5-Amino-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide |

TABLE 1-continued

| Example | Structure | Name |
|---|---|---|
| 32 | 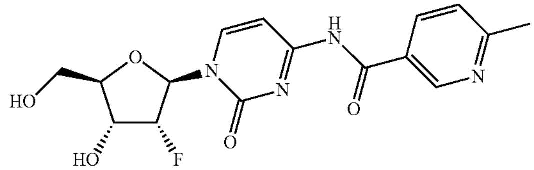 [SMILES: Cc1ccc(C(=O)Nc2ccn([C@@H]3O[C@H](CO)[C@@H](O)[C@H]3F)c(=O)n2)cn1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylnicotinamide |
| 33 | 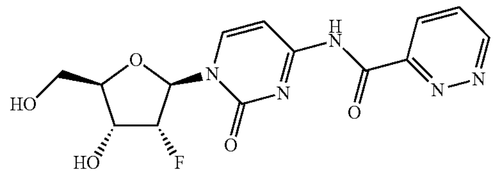 [SMILES: O=C(Nc1ccn([C@@H]2O[C@H](CO)[C@@H](O)[C@H]2F)c(=O)n1)c1cccnn1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)pyridazine-3-carboxamide |
| 34 | 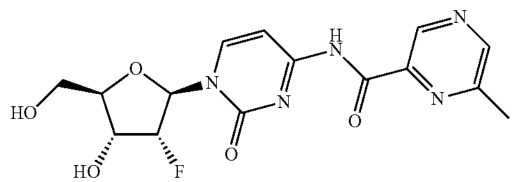 [SMILES: Cc1cncc(C(=O)Nc2ccn([C@@H]3O[C@H](CO)[C@@H](O)[C@H]3F)c(=O)n2)n1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylpyrazine-2-carboxamide |
| 35 | 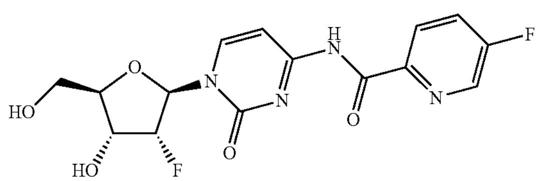 [SMILES: O=C(Nc1ccn([C@@H]2O[C@H](CO)[C@@H](O)[C@H]2F)c(=O)n1)c1ccc(F)cn1] | 5-Fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide |
| 36 | 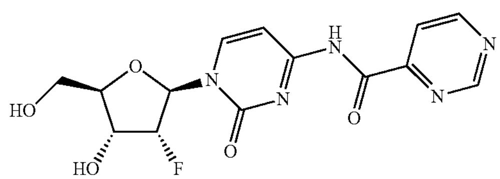 [SMILES: O=C(Nc1ccn([C@@H]2O[C@H](CO)[C@@H](O)[C@H]2F)c(=O)n1)c1ccncn1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)pyrimidine-4-carboxamide |
| 37 | 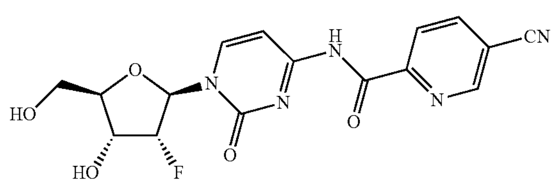 [SMILES: N#Cc1ccc(C(=O)Nc2ccn([C@@H]3O[C@H](CO)[C@@H](O)[C@H]3F)c(=O)n2)nc1] | 5-cyano-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide |
| 38 | 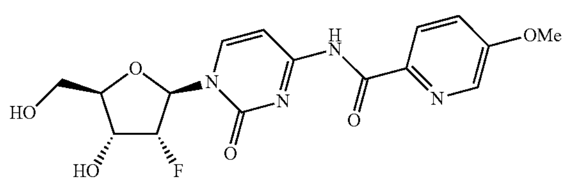 [SMILES: COc1ccc(C(=O)Nc2ccn([C@@H]3O[C@H](CO)[C@@H](O)[C@H]3F)c(=O)n2)nc1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methylpicolinamide |
| 39 | 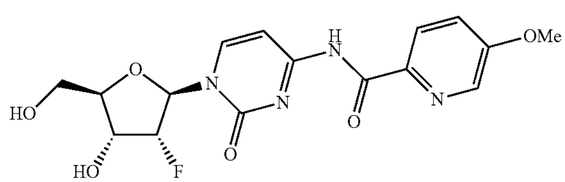 [SMILES: COc1ccc(C(=O)Nc2ccn([C@@H]3O[C@H](CO)[C@@H](O)[C@H]3F)c(=O)n2)nc1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methoxypicolinamide |

TABLE 1-continued

| Example | Structure | Name |
|---|---|---|
| 40 | 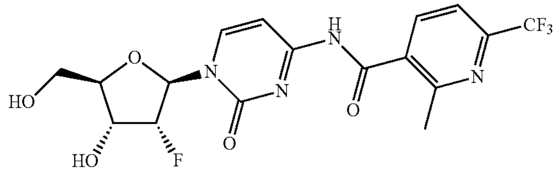 [SMILES: Cc1nc(C(F)(F)F)ccc1C(=O)Nc1ccn([C@@H]2O[C@H](CO)[C@@H](O)[C@H]2F)c(=O)n1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide |
| 41 | 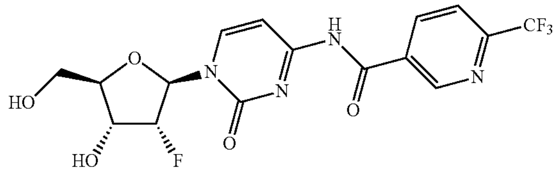 [SMILES: O=C(Nc1ccn([C@@H]2O[C@H](CO)[C@@H](O)[C@H]2F)c(=O)n1)c1ccc(C(F)(F)F)nc1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-(trifluoromethyl)nicotinamide |
| 42 | 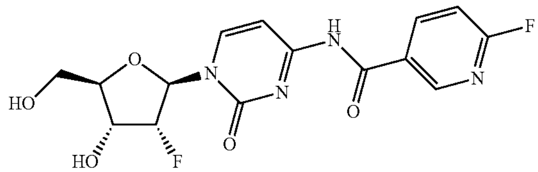 [SMILES: O=C(Nc1ccn([C@@H]2O[C@H](CO)[C@@H](O)[C@H]2F)c(=O)n1)c1ccc(F)nc1] | 6-Fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide |
| 43 | 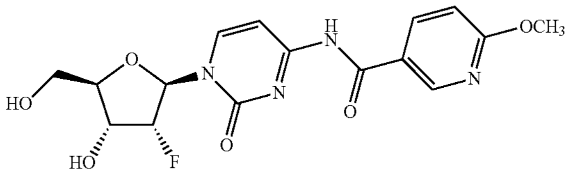 [SMILES: COc1ccc(C(=O)Nc2ccn([C@@H]3O[C@H](CO)[C@@H](O)[C@H]3F)c(=O)n2)cn1] | N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methoxynicotinamide |
| 44 | 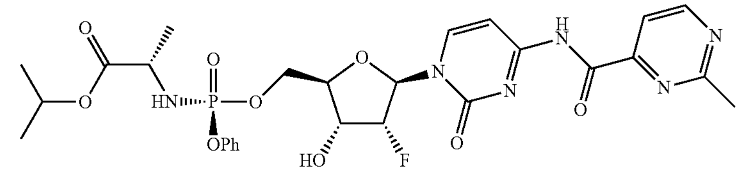 [SMILES: Cc1nccc(C(=O)Nc2ccn([C@@H]3O[C@H](CO[P@@](=O)(N[C@@H](C)C(=O)OC(C)C)Oc4ccccc4)[C@@H](O)[C@H]3F)c(=O)n2)n1] | Isopropyl ((S)-(((2R,3R,4R,5R)-4-fluoro-3-hydroxy-5-(4-(2-methylpyrimidine-4-carboxamido)-2-oxopyridin-1(2H)-yl)tetrahydrofuran-2-yl)methoxy)(phenoxy)phosphoryl)-L-alaninate |

Experimental Example 1: Efficacy Test Against Influenza Virus

In order to examine whether the compounds of Examples exhibit activity against various influenza viruses, the following experiments were carried out.

(1) Preparation of Cells Infected with Influenza Virus

MDCK (Madin-Darby canine kidney) cells were purchased from ATCC (United States), and cultured in a minimal essential medium (MEM) containing 10% fetal bovine serum (FBS). The incubator was maintained at a temperature of 37° C., and the concentration of carbon dioxide was kept at 5%.

Influenza virus A/Puerto Rico/8/34 (H1N1) (hereinafter referred to as "PR8"), A/HongKong/8/68 (H3N2) (hereinafter referred to as "HK"), and B/Lee/40 (hereafter referred to as "Lee") were purchased from ATCC. Influenza viruses PR8 and HK were inoculated into 10-day-old eggs and proliferated at 37° C. MDCK cells were infected with influenza virus Lee and proliferated. At this time, 2 μg/ml of TPCK-trypsin (Sigma, St. Louis, Mo.) was added to serum-free culture medium. The culture temperature was kept at 35° C. Three days after infection, egg allantoic fluids or cell culture media were harvested and centrifuged at 1,000 rpm for 5 minutes to remove cell-derived debris, thereby obtaining proliferated virus. The virus titer was determined by the using hemagglutinin (HA) assay using chicken red blood cells, or by counting the number of viral plaques after infecting fresh MDCK cells with viruses. Each virus was dispensed and stored at 70° C.

(2) Measurement of Cytopathic Effect Reduction

MDCK cells grown sufficiently in a 96-well plate were washed with phosphate-buffered saline (PBS), and then 50-100 plaque forming units (PFU) of influenza viruses were inoculated per well. It was left at 35° C. for an hour so that cells were infected with individual viruses, including PR8, HK, and Lee. After removing uninfected virus by washing with phosphate buffered saline, MEM culture media supplemented with 2 g/ml TPCK-trypsin in the presence of increasing concentrations of each compound were added to the mock-infected or virus-infected cells. On the third day post-infection, the cell viability was determined using 3-(4,5-dimethylthiazol-2-yl)-2,5-dipheyltetrazolimbromide (MTT) [Y. Jang et al., 2016. Antiviral activity of KR-23502 targeting nuclear export of influenza B virus ribonucleoproteins, Antiviral Res 134:77-88].

To briefly summarize the method, the cell culture media were removed and 100 μl of MTT solution (2.5 mg/ml) was added to each well, and the samples were left at 37° C. for 1 hour for sufficient cell lysis. After the reaction was stopped by adding 100 μl of MTT solvent (4 mM HCl, 0.1% Nondet P-40 (NP40) in isopropanol), the absorbance intensity was measured with a spectrophotometer (Model: SpectraMax M3 plate reader from Molecular Devices, Sunnyvale, Calif.) at 540 nm to 690 nm. The 50% cytotoxicity concentration ($CC_{50}$, the concentration of the compound that causes 50% damage of normal cells) and the 50% effective concentration ($EC_{50}$, the concentration at which cytotoxicity caused by viral infection was normalized by 50%) were calculated. As a control group, conventional standard antiviral agents, amantadine hydrochloride (AMT; Sigma), oseltamivir carboxylate (OSV-C; US Biological, Swampscott, Mass.) and ribavirin (RBV; Sigma) were used.

TABLE 2

Anti-influenza virus efficacy of nucleoside or nucleotide derivatives

| | | Anti-Flu activity ($EC_{50}$: μM) | | | Selectivity index | | |
|---|---|---|---|---|---|---|---|
| Example | Toxicity $CC_{50}$ (μM) | FluA H1N1 (PR8) | FluA H3N2 (Hong Kong) | FluB Lee | FluA H1N1 (PR8) | FluA H3N2 (Hong Kong) | FluB Lee |
| 1 | >100.0 | 21.00 | 128.00 | 8.60 | >14.3 | >23.4 | >34.9 |
| 2 | >100.0 | 1.7 | 1.00 | 2.20 | >176.5 | >300 | >136.4 |
| 3 | >100.0 | 2.5 | 1.90 | 2.40 | >40.0 | >52.6 | >41.7 |
| 4 | >100.0 | 1.8 | 2.00 | 1.90 | >166.7 | >150.0 | >157.9 |
| 5 | >100.0 | 2.2 | 1.90 | 2.10 | >136.4 | >157.9 | >142.9 |
| 7 | >100.0 | 14.1 | 15.40 | 9.40 | >7.1 | >6.5 | >10.6 |
| 9 | >100.0 | 8.8 | 4.40 | 6.10 | >11.4 | >22.7 | >16.4 |
| 10 | >100.0 | 16.1 | 11.40 | 9.80 | >6.2 | >8.8 | >10.2 |
| 12 | >100.0 | 56.9 | 51.70 | 49.10 | >1.8 | >1.9 | >2.0 |
| 13 | >100.0 | 9.1 | 7.10 | 7.80 | >11.0 | >14.1 | >12.8 |
| 14 | >100.0 | 6 | 2.9 | 3.1 | >16.7 | >34.5 | >32.3 |
| 15 | >100.0 | 12 | 6.8 | 8 | >8.3 | 14.7 | 12.5 |
| 17 | >100.0 | 1.7 | 3.30 | 2.40 | >58.8 | >30.3 | >41.7 |
| 18 | >100.0 | 53.4 | 83.00 | 49.30 | >1.9 | >1.2 | >2.0 |
| 19 | >100.0 | 1.4 | 2.00 | <1.2 | >71.4 | >50.0 | >83.3 |
| 20 | >100.0 | 9.7 | 18.80 | 19.50 | >10.3 | >5.3 | >5.1 |
| 21 | >100.0 | 20.7 | 27.90 | 22.30 | >4.8 | >3.6 | >4.5 |
| 22 | >100.0 | 20.1 | 36.40 | 24.40 | >5.0 | >2.7 | >4.1 |
| 23 | >100.0 | 6.3 | 8.20 | 6.20 | >15.9 | >12.2 | >16.1 |
| 24 | >100.0 | <1.2 | 2.20 | <1.2 | >83.3 | >45.5 | >83 |
| 25 | >100.0 | 6.5 | 9.50 | 6.10 | >15.4 | >10.5 | >16.4 |
| 27 | >100.0 | 20.1 | 15.70 | 15.60 | >5.0 | >6.4 | >6.4 |
| 28 | >100.0 | 67.5 | 18.00 | 27.80 | >1.5 | >5.6 | >3.6 |
| 29 | >100.0 | 15.4 | 2.60 | 5.60 | >6.5 | >38.5 | >17.9 |
| 30 | >100.0 | 19.5 | 3.50 | 6.50 | >5.1 | >28.6 | >15.4 |
| 33 | >100.0 | 10 | 2.60 | 7.80 | >10.0 | >38.5 | >12.8 |
| 34 | >100.0 | 23.6 | 5.60 | 11.10 | >4.2 | >17.9 | >9.0 |
| 35 | >100.0 | 65.5 | 19.20 | 37.40 | >1.5 | >5.2 | >2.7 |
| 36 | >100.0 | 33.3 | 6.80 | 11.40 | >3.0 | >14.7 | >8.8 |
| 37 | >100.0 | 47.3 | 6.00 | 15.10 | >2.1 | >16.7 | >6.6 |
| 38 | >100.0 | 56.1 | 40.0 | 52.2 | >1.8 | >2.5 | >1.9 |
| 41 | >100.0 | 46.3 | 16.0 | 18.9 | >2.2 | >6.3 | >5.3 |
| 42 | >100.0 | 46.2 | 17.9 | 18.3 | >2.2 | >5.6 | >5.5 |
| Gemcitabine | 240.80 | 0.70 | 0.70 | 1.30 | 344 | 344 | 185.2 |
| 2'-FdC | >100.0 | 3.7 | 13.10 | 5.20 | >27 | >7.6 | >19.2 |
| AMT | >100.0 | >100.0 | 1.1 | >100.0 | ND | >90.9 | ND |
| RBV | >100.0 | 42.6 | 21.2 | 40.6 | >2.3 | >4.7 | >2.5 |
| OSV-C | >100.0 | 0.09 | <0.005 | 1.46 | >1,111 | >20,000 | >68.5 |

Experimental Example 2: Anti-Coronavirus Efficacy Test

In order to examine whether the compounds of Examples exhibit various anti-coronavirus activities, the following experiment was conducted.

1. Preparation of Cells Infected with Coronavirus.

Huh-7 (Human hepatoma-7) cells were purchased from JCRB Cell Bank (Japanese Collection of Research Bioresources Cell Bank), and cultured in DMEM (Dulbecco's Modified Eagle's medium) containing 10% fetal bovine serum (FBS). MRC-5 cells were purchased from ATCC (United States), and cultured in MEM (minimal essential medium) containing 10% bovine serum. The incubator was maintained at a temperature of 37° C. and the concentration of carbon dioxide was kept at 5%.

MERS virus (MERS-CoV/KOR/KNIH/002_05_2015) was furnished from the Korea Centers for Disease Control & Prevention. Human coronavirus hCoV 229E, OC43, feline infectious peritonitis virus (FIPV) was purchased from ATCC. MERS virus was allowed to infect Huh-7 cells, which were propagated at 37° C. In the same way, hCoV 229E and OC43 were allowed to infect MRC-5 cells which were proliferated. FIPV proliferated on CRFK cells. Two to three days after the infection, the cell culture media was centrifuged at 3,000 rpm for 20 minutes to remove cell impurities, thereby obtaining a proliferated virus. The virus titer was determined by counting the number of viral plaques after infecting virus on cells used for the propagation of each virus. Each virus was dispensed in a small amount and stored at 70° C.

2. Measurement of Cytopathic Effect Reduction

After Huh-7 (MERS), MRC-5 (hCoV 229E, 043), and CRFK (FIPV) cells grown in 96-well plates were inoculated with respective corresponding viruses per well, the culture media containing the compound of each Example diluted to various concentrations was added to each well. On the third day after the infection, the cell viability was measured using 3-(4,5-dimethylthiazol-2-yl)-2,5-dipheyltetrazolimbromide (MTT). The absorbance intensity was measured with a spectrophotometer (model name: SpectraMax M3 plate reader from Molecular Devices, Sunnyvale, Calif.) at 540 nm to 690 nm. The 50% cytotoxicity concentration ($CC_{50}$, the concentration of the compound that causes 50% damage of normal cells) and the 50% effective concentration ($EC_{50}$, the concentration at which cytotoxicity caused by viral infection was normalized by 50%) were calculated. As a control group, Gemcitabine (Sigma) was used.

Vero cells which were propagated at 37° C. The virus titer was determined by counting the number of viral plaques after infecting MDCK cells with viruses. Each virus was dispensed in a small amount and stored at 70° C.

2. Measurement of Reduction in Viral Infection Using Immunofluorescence Assay

After Vero cells grown in a 96-well plate were inoculated with each dengue virus or zika virus per well, the culture media containing the compound of each Example diluted to various concentrations was added to each well. On the third

TABLE 3

Anti-coronavirus efficacy of nucleoside or nucleotide derivatives

| | Coronaviruses | | | | | | | | | | | |
|---|---|---|---|---|---|---|---|---|---|---|---|---|
| | MERS-CoV | | | hCoV (229E) | | | hCoV (OC43) | | | FIPV | | |
| Example | $CC_{50}$ (μM) | $EC_{50}$ (μM) | SI | $CC_{50}$ (μM) | $EC_{50}$ (μM) | SI | $CC_{50}$ (μM) | $EC_{50}$ (μM) | SI | $CC_{50}$ (μM) | $EC_{50}$ (μM) | SI |
| 1 | >100 | 10.4 | >9.62 | >100 | 4.6 | >21.74 | >100 | 76 | >1.32 | 56 | 25 | 2.24 |
| 2 | >100 | 1.8 | >55.56 | >100 | 0.8 | >125.0 | >100 | >100 | ND | >100 | 9.1 | >10.99 |
| 3 | >100 | 8.9 | >11.24 | >100 | 1.8 | >55.56 | >100 | >100 | ND | >100 | 24 | >4.17 |
| 4 | >100 | 2.2 | >45.45 | >100 | 11.1 | >9.01 | >100 | >100 | ND | >100 | 8.1 | >12.35 |
| 5 | >100 | 1.4 | >71.43 | >100 | 8.9 | >11.24 | >100 | 17.2 | 5.81 | >100 | 8.5 | >11.76 |
| 7 | | | | >100 | 17.6 | >5.68 | >100 | >100 | ND | >100 | 77 | >1.30 |
| 9 | | | | >100 | 2.4 | >41.67 | >100 | >100 | ND | >100 | 18 | >5.56 |
| 10 | | | | >100 | 7.4 | >13.51 | >100 | >100 | ND | 92 | 21 | 4.38 |
| 12 | | | | >100 | 12.2 | >8.20 | | | | | | |
| 13 | | | | >100 | 5.8 | >17.24 | | | | | | |
| 27 | 56.60 | 20.9 | 2.71 | | | | | | | | | |
| 28 | >100 | <100 | ND | | | | | | | | | |
| 29 | >100 | <100 | ND | | | | | | | | | |
| 30 | >100 | <100 | ND | | | | | | | | | |
| 31 | >100 | <100 | ND | | | | | | | | | |
| 32 | >100 | <100 | ND | | | | | | | | | |
| 33 | >100 | <100 | ND | | | | | | | | | |
| 34 | >100 | <100 | ND | | | | | | | | | |
| 35 | >100 | <100 | ND | | | | | | | | | |
| 36 | >100 | <100 | ND | | | | | | | | | |
| 37 | >100 | <100 | ND | | | | | | | | | |
| Gemcitabine | >100 | 1.10 | 90.91 | >100 | 0.44 | 227.27 | | | | 92 | 21 | 4.38 |

Experimental Example 3: Anti-Mosquito-Mediated Virus (Dengue, Zika, Chikungunya) Efficacy Test In order to examine whether the compounds of Examples exhibit various anti-mosquito-mediated virus activities, the following experiments were conducted.

1. Preparation of Cells Infected with Flaviviruses and Alphaviruses.

Vero (African green monkey kidney) cells were purchased from ATCC (United States), and cultured in DMEM containing 10% bovine serum. The incubator was maintained at a temperature of 37° C., and the concentration of carbon dioxide was kept at 5%.

Dengue virus New Guinea C (NGC) belonging to the genus Flavivirus (hereinafter referred to as "DENV") was purchased from the National Collection of Pathogenic Viruses (NCPV, UK). Zikavirus (MR766) was purchased from ATCC (United States). Chikungunya virus, belonging to the genus Alphavirus, was a domestic patient-isolated strain and was purchased from the National Pathogen Resources Bank of the Korea Centers for Disease Control & Prevention. Flavivirus and alphavirus were allowed to infect day after the infection, the infected cells were analyzed by immunofluorescence staining using 4G2 monoclonal antibody that shows cross-reaction to flavivirus membrane proteins. Fluorescence values were measured using Operetta (PerkinElmer) which is an image analysis device.

3. Measurement of Cytopathic Effect Reduction

After Vero cells grown in a 96-well plate were inoculated with Chikungunya virus per well, the culture media containing the compound of each Example diluted to various concentrations was added to each well. On the third day after the infection, the cell viability was measured using 3-(4,5-dimethylthiazol-2-yl)-2,5-dipheyltetrazolimbromide (MTT). The absorbance intensity was measured with a spectrophotometer (model name: SpectraMax M3 plate reader from Molecular Devices, Sunnyvale, Calif.) at 540 nm to 690 nm. The 50% cytotoxicity concentration ($CC_{50}$, the concentration of the compound that causes 50% damage of normal cells) and the 50% effective concentration ($EC_{50}$, the concentration at which cytotoxicity caused by viral infection was normalized by 50%) were calculated. As a control group, Chloroquine (Sigma) was used.

TABLE 4

Anti-mosquito-mediated virus efficacy of nucleoside or nucleotide derivatives

| | Flavivirus | | | | | | Alphavirus | | |
|---|---|---|---|---|---|---|---|---|---|
| | DENV | | | ZIKV | | | CHIKV | | |
| Example | CC$_{50}$ (μM) | EC$_{50}$ (μM) | SI | CC$_{50}$ (μM) | EC$_{50}$ (μM) | SI | CC$_{50}$ (μM) | EC$_{50}$ (μM) | SI |
| 1 | >100 | 3.42 | >29.24 | | | | | | |
| 2 | >100 | 0.72 | >138.89 | | | | | | |
| 3 | >100 | 1.87 | >53.48 | | | | | | |
| 4 | >100 | 0.71 | >140.85 | | | | | | |
| 5 | >100 | 0.94 | >106.38 | | | | | | |
| 7 | >100 | 15.65 | >6.39 | | | | | | |
| 9 | >100 | 1.34 | >74.63 | | | | | | |
| 10 | >100 | 2.53 | >39.53 | | | | | | |
| 12 | >100 | 6.16 | >16.23 | | | | | | |
| 13 | >100 | 1.98 | >50.51 | | | | | | |
| 17 | 58.9 | <1.2 | >49.08 | | | | | | |
| 18 | 11.1 | 35.5 | 0.31 | | | | | | |
| 19 | <1.2 | <1.2 | ND | | | | | | |
| 20 | 75.9 | 1.6 | 47.44 | | | | | | |
| 21 | >100 | 1.3 | >76.92 | | | | | | |
| 22 | <1.2 | <1.2 | ND | | | | | | |
| 23 | <1.2 | <1.2 | ND | | | | | | |
| 24 | 55.35 | <1.2 | >46.12 | | | | | | |
| 25 | 29.5 | <1.2 | >24.58 | | | | | | |
| 26 | >100 | 57.7 | >1.73 | | | | | | |
| 27 | 64.44 | 13.68 | 4.71 | >100 | >100 | ND | >100 | >100 | ND |
| 28 | >100 | 25.33 | >3.95 | >100 | >100 | ND | >100 | >100 | ND |
| 29 | >100 | >100 | ND | >100 | >100 | ND | >100 | 23.97 | >4.17 |
| 30 | >100 | 77.9 | >1.28 | >100 | >100 | ND | >100 | 62.45 | >1.60 |
| 31 | >100 | >100 | ND | >100 | 57.59 | >1.74 | | | |
| 33 | >100 | >100 | ND | >100 | >100 | ND | >100 | 86.37 | >1.16 |
| 36 | >100 | >100 | ND | >100 | >100 | ND | >100 | 57.74 | >1.73 |
| 37 | >100 | >100 | ND | >100 | >100 | ND | >100 | 51.73 | >1.93 |

LC-MS (ESI, m/z)=749.2 (M+H$^+$)

Step 3: Compound (120 mg, 0.160 mmol) obtained from step 2 was dissolved in THF (0.8 ml) and cooled to −5° C. After slowly adding 0.17 ml of TBAF 1M in THF, the mixture was stirred at the same temperature for 20 minutes. Water was added to the reaction solution, diluted with EtOAc, and then washed with water for 3 times. The organic layer was dried over Na$_2$SO$_4$, concentrated under reduced pressure, and then purified by column chromatography to afford the desired product(60 mg) as a white solid.

LC-MS (ESI, m/z)=635.0 (M+H$^+$)

The above Examples are summarized by structure and name in Table 1 below.

Experimental Example 1: Efficacy Test Against Influenza Virus

In order to examine whether the compounds of Examples exhibit activity against various influenza viruses, the following experiments were carried out.

(1) Preparation of Cells Infected with Influenza Virus

MDCK (Madin-Darby canine kidney) cells were purchased from ATCC (United States), and cultured in a minimal essential medium (MEM) containing 10% fetal bovine serum (FBS). The incubator was maintained at a temperature of 37° C., and the concentration of carbon dioxide was kept at 5%.

Influenza virus A/Puerto Rico/8/34 (H1N1) (hereinafter referred to as "PR8"), A/HongKong/8/68 (H3N2) (hereinafter referred to as "HK"), and B/Lee/40 (hereafter referred to as "Lee") were purchased from ATCC. Influenza viruses PR8 and HK were inoculated into 10-day-old eggs and proliferated at 37° C. MDCK cells were infected with influenza virus Lee and proliferated. At this time, 2 μg/ml of TPCK-trypsin (Sigma, St. Louis, Mo.) was added to serum-free culture medium. The culture temperature was kept at 35° C. Three days after infection, egg allantoic fluids or cell culture media were harvested and centrifuged at 1,000 rpm for 5 minutes to remove cell-derived debris, thereby obtaining proliferated virus. The virus titer was determined by the using hemagglutinin (HA) assay using chicken

The invention claimed is:

1. A compound represented by the following Chemical Formula 1, a racemate thereof, a stereoisomer thereof, or a pharmaceutically acceptable salt thereof:

[Chemical Formula 1]

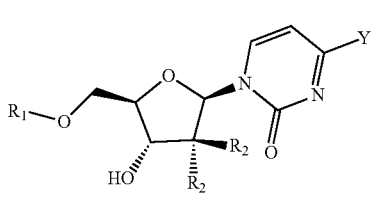

in the Chemical Formula 1,
Y is heterocyclyl or —NHC(O)R$_3$;
R$_1$ is hydrogen or

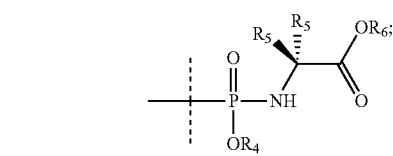

$R_2'$ is hydrogen or halo;
$R_2''$ is halo;
$R_3$ is heteroaryl wherein the heteroaryl is unsubstituted, or 1 to 4 hydrogens thereof are substituted with a substituent selected from the group consisting of halo, amino, cyano, nitro, azido, thiol, hydroxy, $C_{1-6}$ alkyl, $C_{1-6}$ haloalkyl, $C_{1-6}$ aminoalkyl, $C_{1-6}$ hydroxyalkyl, $C_{1-6}$ dihydroxyalkyl, $C_{1-6}$ alkoxy, $C_{3-6}$ cycloalkyl, heterocyclyl, $C_{1-3}$ alkoxy-$C_{1-3}$ alkyl and aryl), wherein the $C_{3-6}$ cycloalkyl or heterocyclyl is optionally substituted with one to three of $C_{1-6}$ alkyl, hydroxy, oxo, $C_{1-6}$ hydroxyalkyl, halo, cyano, nitro, $C_{1-6}$ haloalkyl, $C_{1-6}$ alkoxy, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl, di($C_{1-6}$ alkyl)carbamoyl or $C_{1-3}$ alkoxy-$C_{1-3}$ alkyl;
$R_4$, $R_5$ and $R_6$ are each independently hydrogen, $C_{1-6}$ alkyl, $C_{1-6}$ haloalkyl, aryl or heteroaryl, wherein the aryl or heteroaryl is optionally substituted with one to three of $C_{1-6}$ alkyl, $C_{1-6}$ alkoxy, $C_{1-3}$ alkoxy-$C_{1-3}$ alkyl, $C_{1-6}$ hydroxyalkyl, $C_{1-6}$ haloalkyl, halo, cyano, pyrazinyl, hydroxy, oxo, nitro, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl, di($C_{1-6}$ alkyl)carbamoyl or $C_{1-6}$ alkylsulfonyl;
the halo is F, Cl, Br or I;
the heterocyclyl is tetrahydropyranyl, tetrahydrofuranyl, dihydrofuranyl, dihydropyranyl, dioxanyl, dithianyl, dioxolanyl, imidazolidinyl, imidazolinyl, pyrrolinyl, oxetanyl, piperidinyl, piperazinyl, morpholinyl, thiomorpholinyl, dioxothiomorpholinyl, dioxotetrahydrothiophenyl, dioxothiolanyl, oxopiperidinyl, oxopyrrolidinyl, oxoimidazolidinyl or oxooxazolidinyl, and
the heteroaryl is in the form of a 5- to 10-membered single ring containing one or more heteroatoms selected from the group consisting of nitrogen, oxygen, sulfur or a combination thereof.

2. The compound, the racemate thereof, the stereoisomer thereof, or the pharmaceutically acceptable salt thereof according to claim 1, wherein
Y is heterocyclyl or —NHC(O)$R_3$;
$R_1$ is hydrogen or

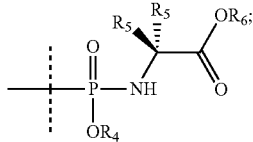

$R_2'$ is hydrogen or halo;
$R_2''$ is halo;
$R_3$ is heteroaryl wherein the heteroaryl is unsubstituted, or 1 to 4 hydrogens thereof are substituted with a substituent selected from the group consisting of halo, amino, cyano, nitro, azido, thiol, hydroxy, $C_{1-4}$ alkyl, $C_{1-4}$ haloalkyl, $C_{1-4}$ aminoalkyl, $C_{1-4}$ hydroxyalkyl, $C_{1-4}$ dihydroxyalkyl, $C_{3-4}$ cycloalkyl, $C_{1-4}$ alkoxy, heterocyclyl, $C_{1-3}$ alkoxy-$C_{1-3}$ alkyl and aryl), wherein the $C_{3-4}$ cycloalkyl or the heterocyclyl is optionally substituted with one to three of $C_{1-4}$ alkyl, hydroxy, oxo, $C_{1-4}$ hydroxyalkyl, halo, cyano, nitro, $C_{1-4}$ haloalkyl, $C_{1-4}$ alkoxy, formyl, $C_{1-4}$ alkylformyl, carboxy, $C_{1-4}$ alkylcarboxy, amino, $C_{1-4}$ alkylamino, di($C_{1-4}$ alkyl)amino, carbamoyl, $C_{1-4}$ alkylcarbamoyl, di($C_{1-4}$ alkyl)carbamoyl or $C_{1-3}$ alkoxy-$C_{1-3}$ alkyl;
$R_4$, $R_5$ and $R_6$ are each independently hydrogen, $C_{1-4}$ alkyl, $C_{1-4}$ haloalkyl, aryl or heteroaryl, wherein the aryl and the heteroaryl is optionally substituted with one to three of $C_{1-6}$ alkyl, $C_{1-6}$ alkoxy, $C_{1-3}$ alkoxy-$C_{1-3}$ alkyl, $C_{1-6}$ hydroxyalkyl, $C_{1-6}$ haloalkyl, halo, cyano, pyrazinyl, hydroxy, oxo, nitro, formyl, $C_{1-4}$ alkylformyl, carboxy, $C_{1-6}$ alkylcarboxy, amino, $C_{1-4}$ alkylamino, di($C_{1-4}$ alkyl)amino, carbamoyl, $C_{1-4}$ alkylcarbamoyl, di($C_{1-4}$ alkyl)carbamoyl or $C_{1-4}$ alkylsulfonyl;
the halo is F, Cl, Br or I;
the heterocyclyl is in the form of a 3- to 10-membered single or fused ring containing one or more heteroatoms selected from the group consisting of nitrogen, oxygen, sulfur or a combination thereof, and the heteroaryl is in the form of a 5- to 10-membered single ring containing one or more heteroatoms selected from the group consisting of nitrogen, oxygen, sulfur or a combination thereof.

3. The compound, the racemate thereof, the stereoisomer thereof, or the pharmaceutically acceptable salt thereof according to claim 1, wherein
$R_3$ is pyridinyl, pyrimidinyl, pyrazinyl, pyridazinyl or triazinyl wherein the pyridinyl, pyrimidinyl, pyrazinyl, pyridazinyl or triazinyl is unsubstituted, or 1 to 4 hydrogens thereof are substituted with a substituent selected from the group consisting of halo, amino, cyano, nitro, azido, thiol, hydroxy, $C_{1-4}$ alkyl, $C_{1-4}$ haloalkyl, $C_{1-4}$ aminoalkyl, $C_{1-4}$ hydroxyalkyl, $C_{1-4}$ dihydroxyalkyl, $C_{3-4}$ cycloalkyl, $C_{1-4}$ alkoxy, heterocyclyl, $C_{1-3}$ alkoxy-$C_{1-3}$ alkyl and aryl), wherein $C_{3-4}$ cycloalkyl or the heterocyclyl is optionally substituted with one to three $C_{1-4}$ alkyl, hydroxy, oxo, halo or $C_{1-4}$ haloalkyl;
the aryl is phenyl, wherein the aryl is optionally substituted with one to three $C_{1-4}$ alkyl, $C_{1-4}$ haloalkyl, halo, hydroxy or oxo.

4. The compound, the racemate thereof, the stereoisomer thereof, or the pharmaceutically acceptable salt thereof according to claim 1, wherein
Y is oxopyrrolidinyl, oxoimidazolidinyl or —NHC(O)$R_3$, wherein the oxopyrrolidinyl and oxoimidazolidinyl are unsubstituted, or 1 to 3 hydrogens thereof are substituted with a substituent selected from the group consisting of fluoro, methyl and trifluoromethyl; and
$R_3$ is pyridinyl, pyrimidinyl, pyrazinyl or pyridazinyl wherein the pyridinyl, pyrimidinyl, pyrazinyl or pyridazinyl is unsubstituted, or 1 to 4 hydrogens are substituted with a substituent selected from the group consisting of fluoro, chloro, methyl, cyano, nitro, amino, methoxy, trifluoromethyl and phenyl.

5. The compound, the racemate thereof, the stereoisomer thereof, or the pharmaceutically acceptable salt thereof according to claim 1, wherein
Y is oxopyrrolidinyl, oxoimidazolidinyl, nicotinoylamino, picolinoylamino, fluoronicotinoylamino, methylnicotinoylamino, pyridazinylcarbonylamino, fluoropicolinoylamino, methyl picolinoylamino or trifluoromethylnicotinoylamino.

6. The compound, the racemate thereof, the stereoisomer thereof, or the pharmaceutically acceptable salt thereof according to claim 1, wherein the compound of Chemical Formula 1 is selected from the group consisting of:
1) N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide;

2) N-(1-((2R,4R,5R)-3,3-difluoro-hydroxy-5-(hydroxymethyl)tetrahydrofuran-2-yl)-2-oxo-1,2-dihydropyrimidin-4-yl)picolinamide;
3) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-fluoronicotinamide;
4) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylnicotinamide;
5) N-(1-((2R,4R,5R)-3,3-difluoro-4-hydroxy-5-(hydroxymethyl)tetrahydrofuran-2-yl)-2-oxo-1,2-dihydropyrimidin-4-yl)pyridazine-3-carboxamide;
6) N-(1-((2R,4R,5R)-3,3-difluoro-4-hydroxy-5-(hydroxymethyl)tetrahydrofuran-2-yl)-4-(2-oxoimidazolidin-1-yl)pyrimidin-2(1H)-one;
7) N-(1-((2R,4R,5R)-3,3-difluoro-4-hydroxy-5-(hydroxymethyl)tetrahydrofuran-2-yl)-4-(2-oxopyrrolidin-1-yl)pyrimidin-2(1H)-one;
8) N-(1-((2R,4R,5R)-3,3-difluoro-4-hydroxy-5-(hydroxymethyl)tetrahydrofuran-2-yl)-4-(3-methyl-2-oxoimidazolidin-1-yl)pyrimidin-2(1H)-one;
9) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-fluoropicolinamide;
10) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methylpicolinamide;
11) N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide;
12) N-(1-((2R,4R,5R)-3,3-difluoro-4-hydroxy-5-(hydroxymethyl)tetrahydrofuran-2-yl)-2-oxo-1,2-dihydropyrimidin-4-yl)-3-methylpicolinamide;
13) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methylpicolinamide;
14) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-(trifluoromethyl)nicotinamide;
15) N-(1-((2R,4R,5R)-3,3-difluoro-4-hydroxy-5-(hydroxymethyl)tetrahydrofuran-2-yl)-2-oxo-1,2-dihydropyrimidin-4-yl)-1-methyl-1H-pyrazole-4-carboxamide;
16) Isopropyl ((S)-(((2R,3R,5R)-4,4-difluoro-3-hydroxy-5-(4-(nicotinamido)-2-oxopyrimidine-1(2H)-yl)tetrahydrofuran-2-yl)methoxy)(phenoxy)phosphoryl)-L-alaninate;
17) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-phenylpicolinamide;
18) 1-((2R,4R,5R)-3,3-difluoro-4-hydroxy-5-(hydroxymethyl)tetrahydrofuran-2-yl)-4-(3-methyl-2-oxopyrrolidin-1-yl)pyrimidin-2(1H)-one;
19) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-nitropicolinamide;
20) 5-amino-N-(1-((2R,4R,5R)-3,3-difluoro-4-hydroxy-5-(hydroxymethyl)tetrahydrofuran-2-yl)-2-oxo-1,2-dihydropyrimidin-4-yl)picolinamide hydrochloride;
21) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-methoxypicolinamide;
22) N-(1-((2R,4R,5R)-3,3-difluoro-4-hydroxy-5-(hydroxymethyl)tetrahydrofuran-2-yl)-2-oxo-1,2-dihydropyrimidin-4-yl)-6-methoxynicotinamide;
23) 6-Chloro-N-(1-((2R,4R,5R)-3,3-difluoro-4-hydroxy-5-(hydroxymethyl)tetrahydrofuran-2-yl)-2-oxo-1,2-dihydropyrimidin-4-yl)nicotinamide;
24) N-(1-((2R,4R,5R)-3,3-difluoro-4-hydroxy-5-(hydroxymethyl)tetrahydrofuran-2-yl)-2-oxo-1,2-dihydropyrimidin-4-yl)-2-methylpyrimidin-4-carboxamide;
25) N-(1-((2R,4R,5R)-3,3-difluoro-4-hydroxy-5-(hydroxymethyl)tetrahydrofuran-2-yl)-2-oxo-1,2-dihydropyrimidin-4-yl)-5-phenylpicolinamide;
26) N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide;
27) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-phenylpicolinamide;
28) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-phenylpicolinamide;
29) N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methylpyrimidin-4-carboxamide;
30) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-nitropicolinamide;
31) 5-Amino-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide;
32) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylnicotinamide;
33) N-(1-((2S,3R,4R,5R)-3-fluoro-4-hydroxy-5-(hydroxymethyl)tetrahydrofuran-2-yl)-2-oxo-1,2-dihydropyrimidin-4-yl)pyridazine-3-carboxamide;
34) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methylpyrazine-2-carboxamide;
35) 5-Fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide;
36) N-(1-((2S,3R,4R,5R)-3-fluoro-4-hydroxy-5-(hydroxymethyl)tetrahydrofuran-2-yl)-2-oxo-1,2-dihydropyrimidin-4-yl)pyrimidine-4-carboxamide;
37) 5-cyano-N-(1-((2S,3R,4R,5R)-3-fluoro-4-hydroxy-5-(hydroxymethyl)tetrahydrofuran-2-yl)-2-oxo-1,2-dihydropyrimidin-4-yl)picolinamide;
38) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methylpicolinamide;
39) N-(1-((2S,3R,4R,5R)-3-fluoro-4-hydroxy-5-(hydroxymethyl)tetrahydrofuran-2-yl)-2-oxo-1,2-dihydropyrimidin-4-yl)-5-methoxypicolinamide;
40) N-(1-((2S,3R,4R,5R)-3-fluoro-4-hydroxy-5-(hydroxymethyl)tetrahydrofuran-2-yl)-2-oxo-1,2-dihydropyrimidin-4-yl)-2-methyl-6-(trifluoromethyl)nicotinamide;
41) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-(trifluoromethyl)nicotinamide;
42) 6-Fluoro-N-(1-((2S,3R,4R,5R)-3-fluoro-4-hydroxy-5-(hydroxymethyl)tetrahydrofuran-2-yl)-2-oxo-1,2-dihydropyrimidin-4-yl)nicotinamide;
43) N-(1-((2S,3R,4R,5R)-3-fluoro-4-hydroxy-5-(hydroxymethyl)tetrahydrofuran-2-yl)-2-oxo-1,2-dihydropyrimidin-4-yl)-6-methoxynicotinamide; and 44) Isopropyl ((S)-(((2R,3R,4R,5R)-4-fluoro-3-hydroxy-5-(4-(2-methylpyrimidine-4-carboxamido)-2-oxopyridin-1(2H)-yl)tetrahydrofuran-2-yl)methoxy)(phenoxy)phosphoryl)-L-alaninate.

7. A pharmaceutical composition for the treatment of diseases associated with viral infection, comprising the compound of the Chemical Formula 1 set forth in claim 1, the racemate thereof, the stereoisomer thereof, or the pharmaceutically acceptable salt thereof as an active ingredient,
wherein the virus-associated diseases are diseases caused by HIV, HBV, HCV, influenza, picorna, flavi, alpha, phlebovirus, ebola or corona virus.

8. The pharmaceutical composition according to claim 7, further comprising a pharmaceutically acceptable carrier, diluent or excipient.

* * * * *